US011461499B2

(12) United States Patent
Jun et al.

(10) Patent No.: US 11,461,499 B2
(45) Date of Patent: *Oct. 4, 2022

(54) DYNAMIC DATA PROTECTION

(71) Applicant: Healthblock, Inc., Palo Alto, CA (US)

(72) Inventors: Brian Jun, Mountain View, CA (US); Jan T. Liphardt, Palo Alto, CA (US)

(73) Assignee: Enya Inc., Palo Alto, CA (US)

(*) Notice: Subject to any disclaimer, the term of this patent is extended or adjusted under 35 U.S.C. 154(b) by 304 days.

This patent is subject to a terminal disclaimer.

(21) Appl. No.: 16/824,223

(22) Filed: Mar. 19, 2020

(65) Prior Publication Data
US 2020/0349288 A1    Nov. 5, 2020

Related U.S. Application Data

(63) Continuation of application No. 16/400,030, filed on Apr. 30, 2019.

(51) Int. Cl.
*G06F 21/62* (2013.01)
*G16H 10/60* (2018.01)

(52) U.S. Cl.
CPC ...... *G06F 21/6263* (2013.01); *G06F 21/6254* (2013.01); *G16H 10/60* (2018.01)

(58) Field of Classification Search
CPC .. G06F 21/6263; G06F 21/6254; G16H 10/60
See application file for complete search history.

(56) References Cited

U.S. PATENT DOCUMENTS 5,852,811 A    12/1998 Atkins
6,456,979 B1    9/2002 Flagg
(Continued)

FOREIGN PATENT DOCUMENTS

DE    102014221969    7/2017
EP    1600876 A1 * 11/2005    ........... G06F 19/322

OTHER PUBLICATIONS

Gantt, Gordon Jr. "Hacking Health Care: authentication security in the age of meaningful use." Journal of Law and Health 27.2: 232(27). Cleveland Marshall College of Law. (Jul. 2014-Sep. 2014) (Year: 2014).*

(Continued)

*Primary Examiner* — Linh Giang Le
(74) *Attorney, Agent, or Firm* — Patrick E. Caldwell, Esq.; The Caldwell Firm, LLC

(57) ABSTRACT

Methods, systems and computer program products for health data protection. Embodiments commence upon receiving a data access request message from a participant in a health ecosystem. The data access request message comprises an indication of one or more health data sets that are held by or at least potentially of interest to the participant. System components are configured to receive the message and to identify the participant. Based on parameter values corresponding to a data protection policy of the participant, a data protection scheme is generated. The scheme includes parameter values derived from the data protection policy. The parameter values of the scheme are used to generate a variation of the health data set that is formed by applying one or more data anonymization, data obfuscation or other data protection techniques to the health data set. A balance among the parameters is calculated so as to achieve a desired outcome.

20 Claims, 10 Drawing Sheets

(56) References Cited

U.S. PATENT DOCUMENTS

| | | | |
|---|---|---|---|
| 7,197,642 B2 | 3/2007 | Walmsley | |
| 7,392,201 B1 | 6/2008 | Binns et al. | |
| 7,685,007 B1 | 3/2010 | Jacobson | |
| 2002/0052761 A1 | 5/2002 | Fey et al. | |
| 2003/0009355 A1 | 1/2003 | Gupta | |
| 2003/0036081 A1 | 2/2003 | Adorjan et al. | |
| 2005/0091101 A1* | 4/2005 | Epling | G06Q 50/265 705/26.1 |
| 2005/0208941 A1 | 9/2005 | Ordille et al. | |
| 2005/0234742 A1 | 10/2005 | Hodgdon | |
| 2005/0255458 A1 | 11/2005 | Polansky | |
| 2005/0282213 A1 | 12/2005 | Halle | |
| 2006/0147947 A1 | 7/2006 | Apfeld et al. | |
| 2008/0228765 A1 | 9/2008 | Kenedy et al. | |
| 2009/0094065 A1 | 4/2009 | Hyde et al. | |
| 2010/0311813 A1 | 12/2010 | Kerner et al. | |
| 2011/0235697 A1 | 9/2011 | Fallon | 375/240 |
| 2014/0281511 A1 | 9/2014 | Kaushik | 713/189 |
| 2014/0289536 A1 | 9/2014 | MacCarthy | 713/164 |
| 2014/0359287 A1 | 12/2014 | Veugen | 713/167 |
| 2015/0227697 A1 | 8/2015 | Nelson et al. | |
| 2015/0304331 A1 | 10/2015 | Nakagawa | 726/28 |
| 2016/0328621 A1 | 11/2016 | Negi et al. | |
| 2017/0005787 A1 | 1/2017 | Weaver | |
| 2018/0101697 A1 | 4/2018 | Rane et al. | |
| 2018/0234234 A1 | 8/2018 | Hurley et al. | |
| 2019/0124051 A1 | 4/2019 | Soon-Shiong | |
| 2019/0156426 A1 | 5/2019 | Drucker et al. | |
| 2019/0199509 A1 | 6/2019 | Hoshizuki | |
| 2019/0229907 A1 | 9/2019 | Nicolson et al. | |
| 2020/0195618 A1 | 6/2020 | Linton | |
| 2020/0311299 A1 | 10/2020 | Amar | |

OTHER PUBLICATIONS

"All the Sensors in Your Smartphone, and How They Work", NELD, David, dated Jul. 23, 2017, 6 pages.
"FeatureMatch: A General ANNF Estimation Technique and its Applications", Ramakanth, A., dated Mar. 3, 2014, 2 pages.
"Metal: Blazing Fast Image Processing", Parziale, G., Jan. 5, 2016, 10 pages.
"Photo Editing with Generative Adversarial Networks (Part 1) NVIDIA Developer Blog", Heinrich, G., Apr. 20, 2017, 13 pages.
"PointNet—Deep Hierarchical Feature Learning on Point Sets in a Metric Space", QI, Charles et al., 2017, 2 pages.
"Efficient Variants of the ICP Algorithm", Rusenkeiwicz, S., May 28, 2001, 8 pages.
"PointNetPlusPlus", QI, Charles et al., 2017, 10 pages.
"Siamese Neural Networks for One-shot Image Recognition", Koch, Gregory, 2015, 8 pages.
"SSD: Single Shot MultiBox Detector", Liu, Wei, Dec. 29, 2016, 17 pages.
"Privacy in Pharmacogenetics", Fredrikson, Matthew, "23rd USENIX Security Symposium", dated Aug. 22, 2014, 17 pages.
"Similarity Search in High Dimensions via Hashing", Gionis, Aristides, "Proceedings of the 25th VLDB Conference", dated Sep. 7, 1999, 12 pages.
"Patient Privacy in the Era of Big Data", Kayaalp, Mehmet, "Balkan Med J 2018", dated Sep. 11, 2017, 10 pages.
"The Algorithmic Foundations of Differential Privacy", Dwork, Cynthia, "Foundations of Trends in Theoretical Computer Science", dated Jan. 1, 2014, 281 pages.
"What is Differential Privacy", Green, Matthew, "https://blog.cryptographyengineering.com/2016/06/15/what-is-differential-privacy/", dated Jun. 15, 2016, 8 pages.
"Actively Secure Two-party Computation", Pullonen, Pille, dated May 20, 2013, 101 pages.
"Efficient Multiparty Protocols Using Circuit Randomization", Beaver, Donald, dated Aug. 11, 1991, 13 pages.
"Invasion of Privacy: Tracking Your Online Behavior Across the Web", Lindsey, Nicole, dated Dec. 6, 2017, 8 pages.
"Round And Communication Efficient Unconditionally-Secure Mpc With T<N/3 In Partially Synchronous Network", Choudhury, A et al. dated 2017, 27 pages.
Catching MPC Cheaters: Cunningham, R., et al., dated 2017, 25 pages.

* cited by examiner

DYNAMIC DATA PROTECTION

RELATED APPLICATIONS

The present application is a continuation of, and claims the benefit of priority to co-pending U.S. patent application Ser. No. 16/400,030 titled "DYNAMIC DATA PROTECTION", filed on Apr. 30, 2019 (now U.S. Pat. No. 10,635,837), which is hereby incorporated by reference in its entirety.

FIELD

This disclosure relates to data analytics, and more particularly to techniques for dynamic data protection.

BACKGROUND

The concept of protecting health information can be traced back to the fourth century BC and the Oath of Hippocrates, which describes obligations on health providers to maintain confidentialities that cover provider-patient relationships. This obligation to keep health information confidential is supported in the codes of ethics of various professional associations (e.g., the American Medical Association). Another aspect of health information protection is associated with the privacy rights of the patient. As applied to healthcare, such privacy rights include the patient's right to make decisions about how their personal information (e.g., name, address, etc.) and health information (e.g., treatment history, medications, etc.) are shared. Privacy rights with respect to individual healthcare decisions and health information have been outlined in court decisions, in federal and state statutes, accrediting organization guidelines, and professional codes of ethics.

For example, certain privacy provisions of the federal Health Insurance Portability and Accountability Act of 1996 (HIPAA) are codified as national standards for health information privacy protection in the United States. A third aspect of health information protection corresponds to responsibilities and rules that govern the security of health information. Such security strives to control access to certain health information or ensure its integrity, so as to preserve the aforementioned confidentiality and/or privacy of the information and maintain its utility.

For many years prior to the computing age, compliance with the foregoing health information protection expectations (e.g., as defined by laws, regulations, rules, guidelines, etc.) might be achieved by merely storing handwritten notes and patient charts in a locked filing cabinet. However, in today's modern computing age, vast amounts of health information are stored electronically in many disparate locations and is frequently accessed by large numbers of participants in the health ecosystem. Such participants might include, for example, patients, physicians, hospitals, pharmacies, and pharmaceutical companies.

Each of these participants recognizes the value and benefit of sharing and/or otherwise collaborating over such health data. Sharing health data among participants helps make better decisions that can improve medical outcomes or facilitate other aspects of healthcare such as claims processing, enrolling patients in clinical trials, helping patients to pay for medical procedures, and identifying suitable insurance products. As one example, detailed information about a new drug from a pharmaceutical company is often desired by downstream participants (e.g., pharmacies, hospitals, and physicians) to facilitate better decision-making about administration of the drug to patients. As another example, detailed information about patients' reactions to the drug is desired by upstream participants (e.g., physicians, hospitals, pharmacies, and pharmaceutical companies) so as to improve patient outcomes. As yet another example, a life insurance company may wish to offer services to suitable patient cohorts and may build actuarial and risk models based on a plurality of data from multiple sources.

While sharing of certain health data might be desired by any one or more of the various participants in the ecosystem, such sharing is often constrained by the aforementioned health information protection expectations. In the United States, for example, the Security Rule of HIPAA specifically addresses the handling of protected health information (PHI). Specifically, the Security Rule of HIPAA was established to protect a patient's personally identifiable information (PII) while still allowing health ecosystem participants access to PHI and flexibility in adoption of technologies that facilitate the handling of PHI. HIPAA governs some but not all health information—for example, medical information disclosed by a patient to the public (e.g., via a Facebook page) is not PHI and similarly health information disclosed by a consumer to an insurance provider (e.g., smoking status) is also not PHI, since there is no patient-doctor relationship between those parties. Despite not always falling under the purview of HIPAA, patients, consumers, insurance companies, banks, and other sources and users of medical information all have strong incentives to be good stewards of sensitive information. Other jurisdictions, such as China, Vietnam, and Singapore, all have their own specific rules and regulations about health data, however in general, all countries, people, and businesses have an interest in protecting sensitive information.

This situation becomes more complicated when data are transmitted over the Internet. In the face of massive volumes of data that can now be transferred over the Internet, various laws, regulations, guidelines, and other types of governance have been established pertaining to the use of data (e.g., non-PHI, PII, non-PII, etc.) in consideration of an individual's privacy preferences. Although the benefits of sharing data—and the need to comply with information protection expectations—are recognized by the different participants in the health ecosystem, there are tradeoffs between the pursuit of the benefits of sharing data and the need to concurrently comply with information protection expectations and security governance. For example, a physician might be compelled (e.g., by HIPAA) to strictly protect a patient's PII, whereas the actual patient might want to be more liberal or free with respect to sharing PHI that includes some or all of their PII.

Unfortunately, there is no single mechanism that concurrently satisfies the wishes and needs of all participants. Specifically, there are no mechanisms for determining a particular data protection level for a particular participant that not only complies with data protection expectations but also seeks to maximize the benefits derived from the data. Conventional approaches often implement a universal (e.g., "one size fits all") data protection policy. Such policies fail to "fit" all participants, either with respect to maximizing the value of shared data to a participant or with respect to observance of the protection (e.g., confidentiality, privacy, and/or security) expectations pertaining to the data. For example, a data provider might implement a data protection technique that obfuscates certain PII in accordance with a set of local regulations. However, for some participants (e.g., a data consumer in a different jurisdiction), this approach may be too strict, resulting in little to no useful data that are available to the participants. For other participants, this approach may be too loose, resulting in unacceptable risks for the participants. Moreover, "one size fits all" protection techniques are often implemented in a static codebase that is hard to alter.

Changing conditions (e.g., changing laws, changing regulations, changing guidelines, changing privacy tolerances of one or more of the participants, etc.) present challenges at least as pertains to updating the codebase in response to ongoing occurrences of such changes. As an example, a patient who once wanted strict privacy protection (e.g., when the patient was healthy), may begin to want to share more of their PII in their PHI after being diagnosed with a health condition (e.g., so as to receive the benefits of collaborative care or new drugs). What is needed is a way to dynamically customize (e.g., for a particular participant in the health ecosystem) a balance between the anonymity and/or protection of data and the utility or value of the data.

SUMMARY

The present disclosure describes techniques used in systems, methods, and in computer program products for dynamic data protection, which techniques advance the relevant technologies to address technological issues with legacy approaches. More specifically, the present disclosure describes techniques used in systems, methods, and in computer program products for dynamically determining data protection schemes. Certain embodiments are directed to technological solutions for dynamically determining participant-specific policy-based data protection schemes to apply to data that is exchanged over the Internet among two or more participants in a health ecosystem.

The disclosed embodiments modify and improve over legacy approaches. In particular, the herein-disclosed techniques provide technical solutions that address the problems attendant to determining a balance between the protection of data and the benefit derived from the data for a particular health ecosystem participant. Such technical solutions involve specific implementations (i.e., data organization, data communication paths, module-to-module interrelationships, etc.) that relate to the software arts for improving how computers exchange information. More specifically, the herein-disclosed techniques apply dynamically determined participant-specific policy-based data protection schemes to data that is exchanged among health ecosystem computing systems.

Various of the disclosed techniques can be chained into ordered combinations of steps that implement various types of data protection that in turn optimize among several variables to achieve a multi-variable balance point. For example, one policy-based data protection scheme might involve data protection through application of a selected hashing algorithm to achieve a particular desired multi-variable balance point, whereas another policy-based data protection scheme might involve data protection through application of a selected differential privacy algorithm to achieve a different desired multi-variable balance point. As such, implementation of the disclosed techniques serve to overcome long-standing yet unsolved technological problems associated with transforming "clear text" health data into protected health data without diminishing the utility or value that could be derived from use of the health data.

Other aspects of the present disclosure relate to establishing and maintaining Internet-based dynamic data marketplaces in which data sources (e.g., patients and pharmacy chains) transact with data seekers (e.g., scientists, pharmaceutical companies, and insurance companies). For example, two competing pharmaceutical companies may transmit bids to receive specific data from specific patient cohorts. Different patients within those cohorts may have different anonymity preferences, thus allowing the patients to realize higher (or lower) monetary compensation for their data. Aspects of the present disclosure allow market participants to rapidly transmit their anonymity/privacy settings to allow their data matched to data seekers that participate in the Internet marketplace.

Aspects of the present disclosure achieve performance and other improvements in peripheral technical fields including (but not limited to) techniques for data obfuscation and techniques for operation of Internet-based information exchanges.

Further details of aspects, objectives, and advantages of the technological embodiments are described herein, and in the drawings and claims.

BRIEF DESCRIPTION OF THE DRAWINGS

The drawings described below are for illustration purposes only. The drawings are not intended to limit the scope of the present disclosure.

DETAILED DESCRIPTION

Figure 1A:
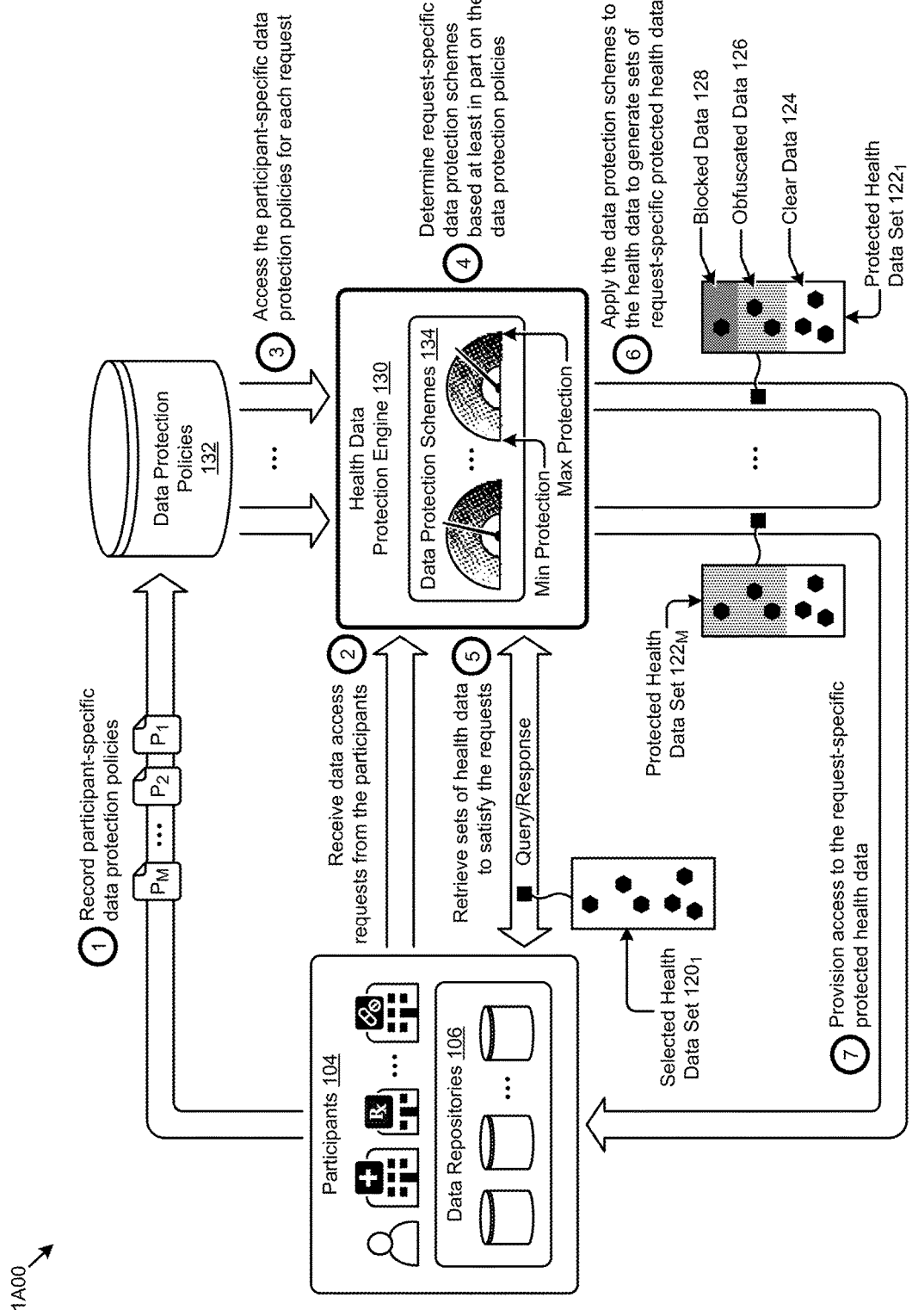
FIG. 1A illustrates a computing environment in which embodiments of the present disclosure can be implemented.

Aspects of the present disclosure solve problems associated with using computer systems for determining a balance between the anonymity/protection of data and the utility or value of the data for a particular health ecosystem participant. These problems are unique to various technological issues associated with determining a balance between the degree of protection of shared healthcare data and the benefits that can be derived from use of the data by a particular health ecosystem participant. Some embodiments are directed to approaches for dynamically determining participant-specific policy-based data protection schemes to apply to data that is exchanged among various health ecosystem participants. The accompanying figures and discussions herein present example environments, systems, methods, and computer program products for dynamically determining data protection schemes.

Overview

Disclosed herein are techniques for dynamically determining policy-based data protection schemes to apply to data sets exchanged by various participants in a health ecosystem. In certain embodiments, each participant in the health ecosystem establishes a participant-specific data protection policy. Such a policy might include policy parameters that indicate a participant's tolerances for data inaccuracies (e.g., match errors due to obfuscation of certain data) and/or data disclosure (e.g., leakage of PII).

Requests for health data issued by the participants are received and processed. Specifically, in response to receiving a data access request by a participant, a data protection policy corresponding to the participant is selected. A data protection scheme to apply to the health data is determined based at least in part on the policy parameters of the data protection policy. The data protection scheme can be based at least in part on the nature of the health data itself, and/or the aforementioned data inaccuracy or disclosure tolerances, and/or other characteristics derived from the policy parameters of the data protection policy, and/or the data access request.

As an example, a particular data protection scheme derived from a data protection policy might specify what types of PII in the health data are to be obfuscated and/or what portions of the health data are to be blocked before giving access to or transmitting the health data. The data protection scheme is applied to the health data to generate an on-demand request-specific and participant-specific set of protected health data that can be accessed by the requesting participant and/or other participants authorized to access the protected health data set. In certain embodiments, the data protection scheme is based at least in part on a privacy "budget" that is either provided by the participant or derived from the participant's data protection policy. In certain embodiments, at least a portion of the data is obfuscated using locality-sensitive hashing algorithms (LSH) and/or differential privacy algorithms. In any of the herein-described embodiments, a data protection scheme serves to balance a particular participant's demand for privacy, security, and anonymity with the scientific or economic value of the data. As used herein, the term "privacy" or "privacy control" refers to the ability of an individual to control who (if anyone) is able to see or track the individual's activities and data. For example, if a transaction is designated as "private" or the transaction is performed in accordance with privacy-preserving rules, then third parties will not be able to determine that the transaction has taken place.

As used herein, the term "anonymity" refers to the ability of individuals to give access to portions of their data or activities without this information being associated with their identity. For example, patients may wish to share genomic information and disease status with scientists without that information being tied to their identity (e.g., an individual's name or other personally-identifiable indicators).

As used herein, the term "security" or "security level" is a value that quantifies the extent to which digital activities and data are protected from threats such as unwanted exposure, disruption, or impersonation.

Definitions and Use of Figures

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale, and that elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Descriptions of Example Embodiments

FIG. 1A illustrates a computing environment 1A00 in which embodiments of the present disclosure can be implemented. As an option, one or more variations of computing environment 1A00 or any aspect thereof may be implemented in the context of the architecture and functionality of the embodiments described herein.

FIG. 1A illustrates aspects pertaining to dynamically determining participant-specific policy-based data protection schemes to apply to data that is exchanged among various health ecosystem participants. Specifically, the figure presents a logical depiction of how the herein disclosed techniques can be used in a computing environment to dynamically determine a balance between the protection of data and the benefit derived from the data for a particular participant and/or a particular data access request in a health ecosystem.

As depicted in FIG. 1A, computing environment 1A00 illustrates a set of representative participants (e.g., participants 104) associated with a health ecosystem. For example, participants 104 might include various patients, medical facilities (e.g., hospitals, clinics, medical offices, etc.), pharmacies, pharmaceutical companies, and/or other participants. The patients and other persons (e.g., physicians, nurses, technicians, billing administrators, scientists, analysts, etc.) associated with the foregoing entities each have various health data they contribute to the health ecosystem and/or desire to access from the health ecosystem. Such health data might be stored in various instances of data repositories 106 that are managed, accessed, and/or otherwise associated with participants 104. The participants 104 have the responsibility to not only manage the health data they contribute to the ecosystem, but to also manage the health data contributed by other participants. Such health data might include the PII of a patient and/or other proprietary information (e.g., confidential drug formulas or test results). For example, the primary care physician (PCP) of a patient owns the records of the patient and must manage its storage, access, and distribution in a way that accommodates the protection expectations of the patient and any governing regulations. As another example, while a hospital and insurance company might each have access to their own instance of a patient's PII (e.g., the same PII), they are often obligated (e.g., by law or regulation) or otherwise compelled to not share it with the other party.

Nonetheless, participants 104 and their corresponding constituents recognize the value and benefit of sharing and/or otherwise collaborating over their health data. As merely examples, such sharing of health data among participants 104 facilitates better decisions by the constituents (e.g., patients, physicians, scientists, analysts, etc.) that in turn result in better outcomes. However, there are compromises to be made to balance pursuit of the benefits of sharing data with respect to the need to concurrently comply with the health data protection expectations of individuals (e.g., patients) and governing authorities (e.g., HIPAA). Such compromises arise at least in part due to the competing relationship between the level of obfuscation of a particular data set and the accuracy of the inferences that can be derived from the data set. For example, a highest level of inference accuracy (e.g., data match accuracy) might be achieved from a data set comprising all clear text, whereas such inference accuracy is diminished when portions of the data set are obfuscated.

Moreover, each of the participants 104 may have a different position as pertains to the competing characteristics of the level of obfuscation of a particular data set and the accuracy of the inferences that can be derived from that data set. For example, consider a pharmaceutical company and a pharmacy. The pharmaceutical company, who might be looking for matches between genes and outcomes, may be able to tolerate a 2% to 3% data matching error, but have no tolerance for any leakage (e.g., sharing) of PII. In comparison, the pharmacy might have a 0% error tolerance (e.g., due to the potential serious or fatal effects of an error) while also having no tolerance for PII leakage. In this example, the pharmaceutical company might be able to derive significantly more inferences from a particular data set than the inferences that could be derived by the pharmacy from the data set, however the overall accuracy of the inferences delivered to the pharmaceutical company will be lower than the accuracy of the inferences delivered to the pharmacy.

The herein disclosed techniques address the foregoing problems attendant to determining a balance between the protection of health data and the benefit derived from the health data for each of the participants 104 by dynamically determining participant-specific policy-based data protection schemes to apply to health data that is exchanged over the Internet by participants 104. As depicted in FIG. 1A, such techniques disclosed herein can be facilitated by a health data protection engine 130 in computing environment 1A00. As shown and described by a set of high order operations, a set of data protection policies 132 (e.g., data protection policy $P_1$, data protection policy $P_2$, ..., data protection policy $P_M$) are recorded for each of the participants 104 (operation 1). Data protection policies 132 comprise parameters that are managed at least in part by participants 104 to specify the data protection characteristics (e.g., data matching error tolerances, data leakage tolerances, etc.) of each respective participant. Health data protection engine 130 has access to data protection policies 132 to facilitate, for example, processing of data access requests from participants 104.

Specifically, when requests from the participants to provision access to certain health data are received at health data protection engine 130 (operation 2), the participant-specific data protection policies of the participants are accessed at data protection policies 132 (operation 3). The parameters constituting the data access requests and the participant-specific data protection policies are analyzed to determine instances of request-specific data protection schemes (operation 4). As used herein, a data protection scheme is a set of attributes that describe how a particular health data set is to be transformed into a protected health data set that can be consumed by one or more participants in a health ecosystem.

For example, the attributes of a data protection scheme might specify which portions of a health data set are to be blocked from access by a participant, which portions of a health data set are to be obfuscated and how such obfuscations are to be performed, and which portions of a health data set can remain as clear text. The attributes of the data protection scheme might be derived from participant-specific tolerances (e.g., as specified in a data protection policy) to protect the privacy of the health data while allowing for accurate inferences to be derived from the health data. The data protection scheme might also be derived from the preferences of a participant serving as a data aggregator (e.g., the provider of health data protection engine 130) or from applicable governing rules, laws, and regulations.

As can be observed in the representative examples of data protection schemes 134, a particular data protection scheme corresponds to a particular position along a data protection continuum that spans a range from a minimum level of data protection (e.g., no data being obfuscated) to a maximum level of data protection (e.g., all data being obfuscated). As earlier mentioned, this range might also be characterized as spanning from a maximum inference accuracy to a minimum inference accuracy, respectively.

Upon receiving data access requests and determining the corresponding request-specific data protection schemes, sets of health data are retrieved to satisfy the requests (operation 5). Specifically, health data protection engine 130 might select the health data sets from the health data in data repositories 106 and issue queries retrieving the health data sets. As an example, a selected health data set $120_1$ might be retrieved from data repositories 106 by health data protection engine 130. The request-specific data protection schemes earlier determined are applied to selected health data set $120_1$ to generate sets of request-specific protected health data (operation 6).

For illustrative purposes, two representative examples of request-specific and participant-specific protected health data sets are shown. Specifically, a protected health data set $122_1$ is presented that indicates a first portion (e.g., blocked data 128) of selected health data set $120_1$ is blocked, a second portion (e.g., obfuscated data 126) of selected health data set $120_1$ is obfuscated, and a remaining portion (e.g., clear data 124) of selected health data set $120_1$ is not transformed. As another example, protected health data set $122_M$ comprises obfuscated data and clear data derived from selected health data set $120_1$ with no portion of selected health data set $120_1$ being blocked. When the request-specific protected health data sets are generated, access to the protected health data sets is provisioned (operation 7). Such access may be provisioned to the participants who issued the data access requests and/or to other participants or classes of participants identified in the requests. In some cases, delivery of the protected health data sets to such authorized participants may be facilitated by health data protection engine 130.

Application of the foregoing techniques and/or other dynamic data protection techniques disclosed herein facilitate improvements in computer functionality that serve to reduce the demand for computer memory, reduce the demand for computer processing power, reduce network bandwidth use, and reduce the demand for intercomponent communication. Specifically, consumption of such computing resources to retrieve, process, and transmit health data that has limited or no benefit (e.g., due to limited or no data matching accuracies) to participants in a health ecosystem can be eliminated when applying the herein-disclosed techniques. Rather, the herein disclosed techniques avoid transmitting health data that has limited or no benefits to participants.

The environment and operations shown and discussed as pertains to FIG. 1A are merely illustrative examples. The computing devices used to carry out the aforementioned operations may differ between computing environment 1A00 and other alternative environments. As one example, the functions and/or operations described above may be carried out in whole or in part by one or more computing devices (e.g., servers, desktop computers, smart phones, etc.) distributed in the alternative environment as shown and discussed as pertains to FIG. 1B.

Figure 1B:
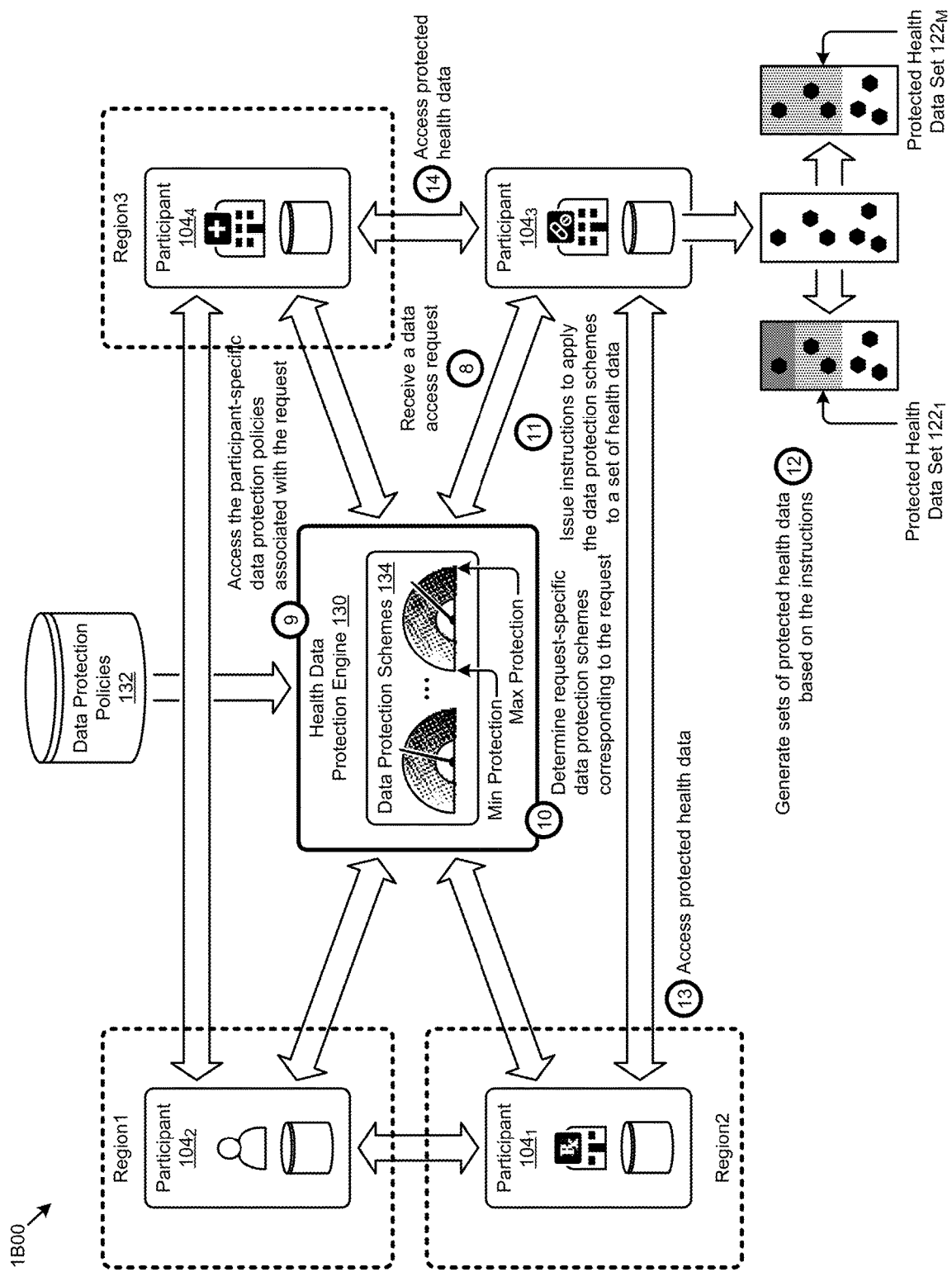
FIG. 1B illustrates a health data exchange environment in which embodiments of the present disclosure can be implemented.

FIG. 1B illustrates a health data exchange environment 1B00 in which embodiments of the present disclosure can be implemented. As an option, one or more variations of health data exchange environment 1B00 or any aspect thereof may be implemented in the context of the architecture and functionality of the embodiments described herein.

FIG. 1B illustrates aspects pertaining to dynamically determining participant-specific policy-based data protection schemes to apply to data that is exchanged among various health ecosystem participants. Specifically, the figure presents a schematic representation of how the herein disclosed techniques can be used in a health data exchange environment (e.g., a health data marketplace) to dynamically generate protected health data sets that can be accessed by a variety of participants in a health ecosystem. Each participant may have differing data protection and data analysis needs and/or priorities. More particularly, a given participant may want to share health data sets with certain participants under a particular commercial arrangement, whereas the same given participant may want to share health data sets with other, different participants under a different commercial arrangement. The health data exchange environment 1B00 supports such user-specific sharing based on participant-specific policies.

As depicted in FIG. 1B, health data exchange environment 1B00 illustrates a set of representative participants associated with a health ecosystem who desire to exchange or otherwise access various healthcare data to facilitate better decisions and/or outcomes. As examples, the participants might include various patients (e.g., participant $104_2$), pharmacies (e.g., participant $104_1$), hospitals or clinics (e.g., participant $104_4$), pharmaceutical companies (e.g., participant $104_3$), and/or other participants. As shown, the participants and/or all or portions of their computing equipment may be situated in different countries or regions (e.g., Region1, Region2, Region3). Such computing equipment, wherever located is configured to communicate with one another (e.g., over the World Wide Web) as well as with health data protection engine 130 earlier described. In this environment, the herein disclosed techniques can facilitate an exchange or marketplace for healthcare data that is protected in accordance with fine-grained request-specific and participant-specific data protection requirements, as described in more detail as follows.

Specifically, in the scenario shown in FIG. 1B, health data protection engine 130 receives a data access request from participant $104_3$ (operation 8). As merely one example, participant $104_3$ might be a pharmaceutical company that desires to provision access to certain data that is protected in accordance with the respective protection policies of a partner hospital (e.g., participant $104_4$) and/or a partner pharmacy (e.g., participant $104_1$). Upon receipt of the data access request, health data protection engine 130 accesses the participant-specific protection policies (e.g., from data protection policies 132) associated with the request (operation 9) and determines one or more request-specific data protection schemes (operation 10).

For example, health data protection engine 130 might access the data protection policies of the aforementioned partner hospital and partner pharmacy and generate a set of respective data protection schemes (e.g., data protection schemes 134) for each entity specified in the data access request.

A set of instructions for execution by participant $104_3$ are then issued by health data protection engine 130 (operation 11). When executed by participant $104_3$, the instructions will apply the earlier determined data protection schemes to a selected set of health data to generate sets of protected health data (operation 12). As shown, a protected health data set $122_1$ and a protected health data set $122_M$ might be generated by computing equipment that is owned or controlled by participant $104_3$ for consumption by participant $104_1$ (e.g., the partner pharmacy) and participant $104_4$ (e.g., the partner hospital), respectively. Each of the participants that are authorized to access the sets of protected health data can then interact with participant $104_3$ to access their respective set of health data that is protected according to their corresponding participant-specific data protection policy. For example, participant $104_1$ can retrieve its protected health data set $122_1$ from data stored by participant $104_3$ (operation 13). Independently, participant $104_4$ can retrieve its protected health data set $122_M$ from participant $104_3$ (operation 14).

Referring again to the instructions for execution by a participant (operation 11), it sometimes occurs that some aspects of data protection are implemented by the health data protection engine 130 before the instructions are issued to a participant. As such, the participant might receive both (1) a set of instructions, and (2) a set of preprocessed health data. The act of issuing instructions to a participant can further include associating specific sets of instructions to be operated over respective specific sets of preprocessed health data.

Referring yet again to the instructions for execution by a participant (operation 11), in some embodiments the foregoing instructions are part of or derived from an app that is downloaded to a computer processor of the participant. By operation of the app, the participant's health data can be preprocessed such that the participant can upload health data in a manner that omits and/or obfuscated personally identifiable information. Moreover, the origin of the uploaded data is verifiable.

Details regarding general approaches to verifying the origin of uploaded data are described in U.S. application Ser. No. 16/364,168 titled "MEASURING AND INCREASING THE QUALITY OF USER-PROVIDED INFORMATION", filed on Mar. 25, 2019, which is hereby incorporated by reference in its entirety.

The components and operations depicted in the foregoing FIG. 1A and FIG. 1B serve to implement various techniques for dynamic, participant-specific and request-specific health data protection. Any of the foregoing operations can be configured to cause a participant-specific and/or request-specific multi-variable balance point, which balance point is formed by particular value settings of security parameters, privacy parameters, scientific value parameters, and economic value parameters. Many such balance points can be configured across the range of the aforementioned security parameters, privacy parameters, scientific value parameters, and economic value parameters. For example, at one extreme, absolute security (and absolute privacy) can be achieved by never digitizing or sharing any information. At this extreme, the information, is both secure and private (cannot be accessed by others), and thus does not add to the corpus of information that might be helpful to science. Being inaccessible to anyone else, it cannot accrue value to anyone else. At this extreme, the security and privacy settings negate the scientific or economic value that could otherwise have been achieved.

At a different extreme, an individual with a significant health condition may want to offer unrestricted medical record access to any and all participants who might be able to use the data to find a cure for the disease. At this extreme, scientific benefit is sought—even at the expense of possible economic value and even at the expense of the degree of individual privacy that might otherwise be available had the individual not freely offered access to their medical records.

At certain other balance points among these variables, a patient might want to give scientists and non-profit institutions partially-restricted access to his or her patient data so as to foster pursuit of scientific benefit. At the same time, the patient may want to collect a fee from pharmaceutical companies that access the patient's data. Using the herein-disclosed techniques, these variables can be balanced based on participant-specific and/or request-specific specifications. Moreover, some variables can be prioritized over other variables. For example, a user might care a great deal about privacy and security, but nevertheless would be willing to sacrifice privacy and security for economic remuneration.

As can now be seen, the components, interconnections and operations of FIG. 1A and FIG. 1B, enable dynamic, fine-grained adjustment of privacy, security, scientific benefit and economic value parameter settings. Moreover, these settings can be automatically bounded based on environmental factors. For example, the settings can be automatically constrained to fall within pre-specified ranges that are applicable to particular environmental situations or conditions. Such constraints might derive from an individual's desires, or might derive from corporate desires, or might derive from country-specific governmental controls. In some cases, constraints arise from temporal considerations (e.g., pertaining to data that has a value that varies over time).

Additional or alternative computer-implemented techniques for carrying out dynamic, participant-specific and request-specific health data protection are disclosed in detail as follows.

Figure 2:
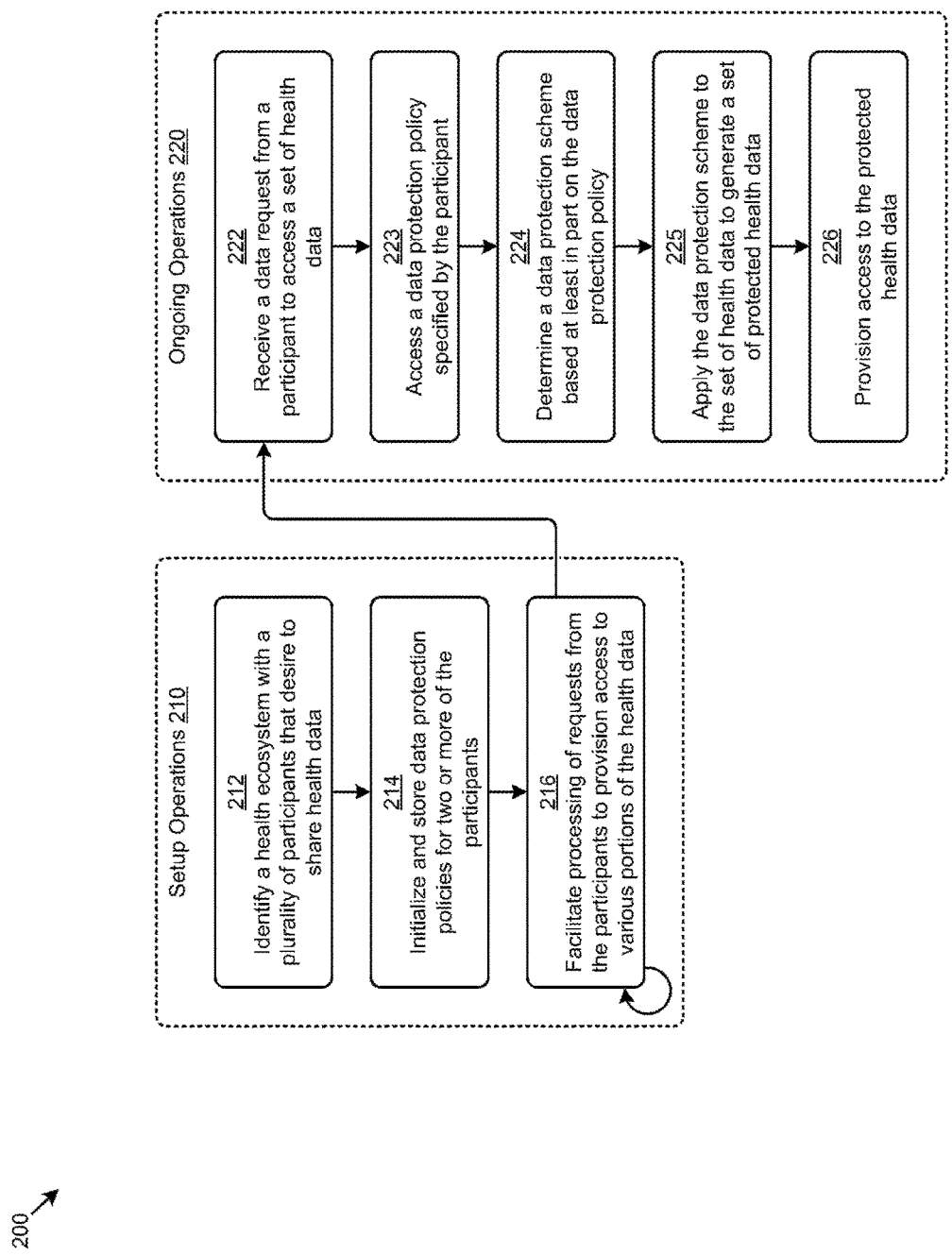
FIG. 2 depicts a dynamic data protection technique as implemented in systems that dynamically determine data protection schemes, according to an embodiment.

FIG. 2 depicts a dynamic data protection technique 200 as implemented in systems that dynamically determine data protection schemes. As an option, one or more variations of dynamic data protection technique 200 or any aspect thereof may be implemented in the context of the architecture and functionality of the embodiments described herein. The dynamic data protection technique 200 or any aspect thereof may be implemented in any environment.

FIG. 2 illustrates aspects pertaining to dynamically determining participant-specific policy-based data protection schemes to apply to data that is exchanged among various health ecosystem participants. Specifically, the figure is presented to illustrate one embodiment of certain steps and/or operations performed over various devices (e.g., user devices, servers, systems, etc.) to facilitate access to health data by a particular participant that is protected in accordance with a data protection policy specified by the participant. As can be observed, the steps and/or operations can be grouped into a set of setup operations 210 and a set of ongoing operations 220.

The setup operations 210 of dynamic data protection technique 200 commence by identifying a health ecosystem that comprises a plurality of participants that desire to share health data (step 212). As an example, the health ecosystem might comprise patients, physicians, pharmacists, scientists, analysts and others associated with various entities (e.g., hospitals, pharmacies, pharmaceutical companies, etc.) that each have data they own and manage that others may have a desire to access. Access to data protection policies associated with each of the participants is initiated (step 214).

A data protection policy may be associated with an individual (e.g., patient, physician, etc.) or an organization (e.g., hospital, company, etc.). A mechanism to facilitate the processing of data access requests from the participants to provision access to various portions of the health data is established (step 216). As an example, one or more instances of a computing agent (e.g., a health data protection engine) might be implemented in the health ecosystem to facilitate such processing of data access requests. As illustrated, the processing of data access requests is a continuous operation at least as compared to the other steps and/or operations in setup operations 210.

The ongoing operations 220 of dynamic data protection technique 200 commence by receiving a data access request from a participant in the health ecosystem to access a set of health data (step 222). The data protection policy of the participant that issued the data access request is accessed (step 223). Based at least in part on the parameters of the data access request and the participant-specific data protection policy, a data protection scheme is determined (step 224).

As earlier described, the data protection scheme describes how the health data set requested by the participant is to be transformed into a protected health data set that can be consumed the participant. The data protection scheme is applied to the health data set to generate a protected health data set for the participant (step 225). In some cases, certain data transformations in accordance with the data protection scheme might be applied at the source (e.g., data repository) of the health data set, whereas other data transformations might be performed after the health data set is retrieved from the source. Access to the participant-specific and request-specific protected health data set that has been dynamically generated is then provisioned (step 226). The access might be provisioned to the participant that issued the data access request and/or to other participants specified in the data access request. In some cases, and as described in more detail herein, a record of the data access request and delivery of protected health data set might be recorded (e.g., in an access ledger).

One embodiment of a system, data flows, and data structures for implementing the dynamic data protection technique 200 and/or other herein disclosed techniques is disclosed as follows.

Figure 3:
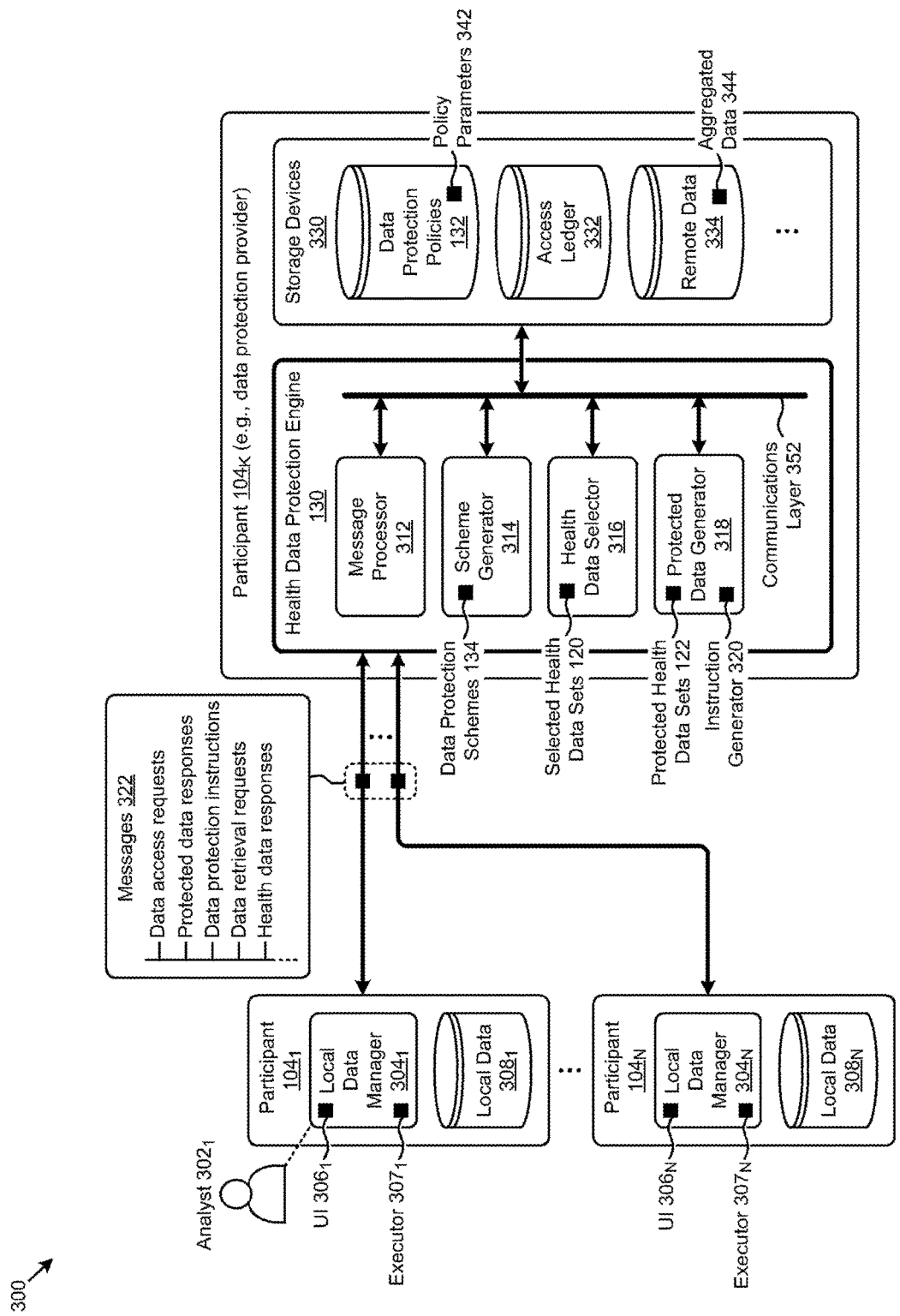
FIG. 3 is a block diagram of a system that implements dynamic determination of data protection schemes, according to an embodiment.

FIG. 3 is a block diagram of a system 300 that implements dynamic determination of data protection schemes. As an option, one or more variations of system 300 or any aspect thereof may be implemented in the context of the architecture and functionality of the embodiments described herein. The system 300 or any aspect thereof may be implemented in any environment.

FIG. 3 illustrates aspects pertaining to dynamically determining participant-specific policy-based data protection schemes to apply to data that is exchanged among various health ecosystem participants. Specifically, the figure is being presented to show one embodiment of certain representative components and associated data structures and data flows implemented in a computing environment to facilitate the herein disclosed techniques. As shown, the components, data flows, and data structures are associated with a set of participants in a health ecosystem. The components, data flows, and data structures shown in FIG. 3 present merely one example partitioning and associated data manipulation approaches. The specific example shown is purely exemplary, and other subsystems, data structures, and/or partitioning are reasonable.

As shown, system 300 comprises an instance of health data protection engine 130 earlier described operating at a participant $104_K$ in the health ecosystem. As merely one example, participant $104_K$ might be an entity (e.g., a data protection provider) in the health ecosystem that facilitates protection and exchange of healthcare data over the participants in the ecosystem. Health data protection engine 130 comprises a message processor 312, a scheme generator 314, a health data selector 316, and a protected data generator 318. A plurality of instances of the foregoing components might operate at a plurality of instances of servers at participant $104_K$ and/or any portion of system 300. Such instances can access each other (e.g., through a communications layer 352) and/or a set of storage devices 330 that store various information that facilitates operation of health data protection engine 130, other components of system 300, and/or any implementations of the herein disclosed techniques.

Various users (e.g., analyst $302_1$) associated with participants (e.g., participant $104_1$, ..., participant $104_N$) in a health ecosystem interact with the user interfaces (e.g., UI $306_1$, ..., UI $306_N$) of certain applications (e.g., local data manager $304_1$, ..., local data manager $304_N$) to send or receive various instances of messages 322 that are received or sent by message processor 312 of health data protection engine 130. In some cases, certain agents or applications (e.g., local data manager $304_1$, ..., local data manager $304_N$) operating at computing devices associated with the participants might send or receive messages to or from health data protection engine 130 without human interaction. One class of messages 322 are data access requests that are issued by the participants to access certain sets of health data. In this case, the data access requests are analyzed by message processor 312 to extract certain parameters that facilitate identification of the participants issuing or otherwise associated with the requests and the health data corresponding to the requests.

The scheme generator 314 uses the foregoing data access request parameters to access the data protection policy of the associated participants from the data protection policies 132 stored at storage devices 330. The parameters (e.g., policy parameters 342) that characterize the participant-specific data protection policies are analyzed by scheme generator 314 to determine respective data protection schemes for the participants and corresponding requests. The data protection schemes 134 generated by scheme generator 314 can be ephemeral (e.g., dynamically determined for each data access request and later discarded) or stored in a set of remote data 334 in the storage devices 330 at participant $104_K$.

Based at least in part on the data access requests, data protection policies, data protection schemes, and/or other information, sets of health data to satisfy the data access requests are selected by health data selector 316. In some cases, certain instances of selected health data sets 120 processed by health data selector 316 might be retrieved from remote data 334. For example, a health data set for a particular data access request might be retrieved from sets of aggregated data 344 stored in remote data 334. Such aggregated data might be generated and stored at participant $104_K$ over time as data access requests are received from other participants. In other cases, certain instances of selected health data sets 120 might be retrieved from the various data repositories (e.g., local data $308_1$, ..., local data $308_N$) of other participants in response to receiving the data access requests. In these cases, the health data selector 316 will invoke one or more data retrieval requests to be issued by message processor 312 as instances of messages 322 to various participants. The corresponding instances of health data responses received as instances of messages 322 by message processor 312 will be processed to deliver the health data sets to health data selector 316.

When the health data sets corresponding to the data access requests have been retrieved, the earlier determined request-specific data protection schemes are applied to the health data sets by protected data generator 318 to generate instances of protected health data sets 122. The dynamically generated participant-specific and request-specific instances of protected health data sets 122 are then delivered as instances of protected data responses by message processor 312 to the participants associated with the respective data access requests. In some cases, certain instances of the protected health data sets 122 might be stored in remote data 334 (e.g., as aggregated data 344) for later access.

In other cases, health data protection engine 130 does not retrieve the health data sets identified by health data selector 316, but instead operational elements of the health data protection engine 130 generates and issues certain data protection instructions to be applied locally over the selected health data sets. As an example, an instruction generator 320 at protected data generator 318 may construct a codebase that, when executed, applies one or more data protection schemes to a target health data set. Instances of such codebases can be packaged and issued as instances of messages 322 to target participants for local execution at, for example, an executor (e.g., at executor $307_1$, . . . , executor $307_N$) implemented at each respective local data manager.

Various attributes pertaining the data access requests, the protected data responses, and/or other information may also be recorded in an access ledger 332 in storage devices 330 for later access. For example, the data recorded in access ledger 332 might be consulted by health data selector 316 when identifying the data sources and/or data repositories from which to retrieve a health data set that can best satisfy a particular data access request.

The foregoing discussions include techniques for determining a data protection scheme based at least in part on a participant-specific data protection policy (e.g., step 224 of FIG. 2), which techniques and data are disclosed in further detail as follows.

Figure 4:
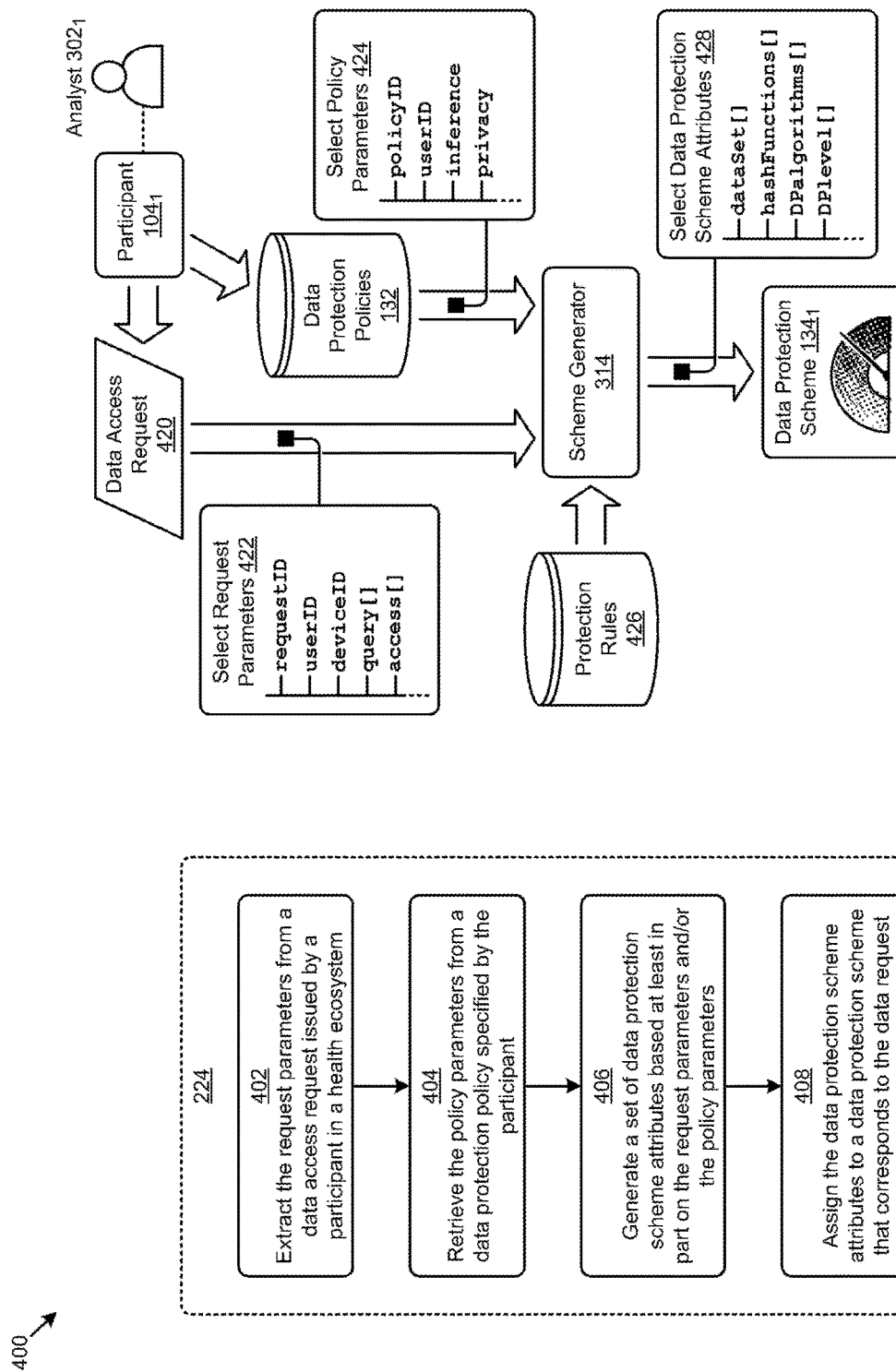
FIG. 4 presents a data protection scheme identification technique as implemented in systems that facilitate dynamic determination of data protection schemes, according to an embodiment.

FIG. 4 presents a data protection scheme identification technique 400 as implemented in systems that facilitate dynamic determination of data protection schemes. As an option, one or more variations of data protection scheme identification technique 400 or any aspect thereof may be implemented in the context of the architecture and functionality of the embodiments described herein. The data protection scheme identification technique 400 or any aspect thereof may be implemented in any environment.

FIG. 4 illustrates aspects pertaining to dynamically determining participant-specific policy-based data protection schemes to apply to data that is exchanged among various health ecosystem participants. Specifically, the figure is presented to illustrate one embodiment of certain steps and/or operations that facilitate determining a data protection scheme based at least in part on a participant-specific data protection policy (e.g., step 224 of FIG. 2). A representative data protection scheme determination scenario is also shown in the figure to illustrate an example application of data protection scheme identification technique 400.

Data protection scheme identification technique 400 commences by extracting one or more request parameters from a data access request issued by a participant in a health ecosystem (step 402). For example, the scenario shown indicates a data access request 420 is issued by analyst $302_1$ associated with participant $104_1$. As depicted in a representative set of select request parameters 422, data access request 420 might comprise parameters that describe a request identifier (e.g., stored in a "request ID" field), a participant or user identifier associated with the issuer of the request (e.g., stored in a "userID" field), a user device identifier (e.g., stored in a "deviceID" field), a set of data management statements and/or data control statements (e.g., stored in a "query[ ]" object), a set of access permissions associated with the request (e.g., stored in an "access[ ]" object), and/or other request parameters.

The aforementioned user device identifier might be associated with a smart phone or laptop computer or desktop computer or any other user device used to issue the data access request. Furthermore, the information codified in the "query[ ]" object serves at least in part to characterize the characteristics (e.g., type, scope, etc.) of the health data being requested. The "access[ ]" object specifies the access permissions corresponding to the health data to be provisioned to various participants in the ecosystem. For example, a data owner may issue a data access request to generate various versions of protected health data that can be accessed by other data consumers in the health ecosystem.

According to data protection scheme identification technique 400, the policy parameters of a data protection policy specified by the participant are retrieved (step 404). For example, the policy parameters might be associated with a data protection policy specified by participant $104_1$ and recorded in data protection policies 132. As depicted in a representative set of select policy parameters 424, a data protection policy might comprise parameters that describe a policy identifier (e.g., stored in a "policyID" field), a participant or user identifier (e.g., stored in a "userID" field), an inference performance indicator (e.g., stored in an "inference" field), a data leakage tolerance indicator (e.g., stored in a "privacy" field), and/or other policy parameters. The inference performance indicator might be, for example, a percentage value (e.g., from 0% to 100%) that indicates the percentage of incorrect data inferences (e.g., matches, predictions, etc.) the participant is willing to tolerate. The privacy budget indicator might be a value from 0 to 100 that indicates a relative level of data leakage the participant is willing to tolerate, where 0 indicates a minimum leakage and 100 indicates a maximum leakage. As earlier described, the inference performance and privacy budget are often related (e.g., competing). As such, one of these policy parameters might even be derived from the other. In this case, merely one of the parameters will be specified in the data protection policy.

Based at least in part on the foregoing request parameters and policy parameters, a set of data protection scheme attributes is generated (step 406). The set of data protection scheme attributes are assigned to a data protection scheme that corresponds to the data access request and the participant that issued the data access request (step 408). As shown, scheme generator 314 consumes the request parameters and policy parameters to generate attributes that are assigned to a data protection scheme $134_1$. In some cases, a set of protection rules 426 are consulted by scheme generator 314 when generating the data protection scheme and its attributes.

A set of rules (e.g., rule base) such as protection rules 426 or any other rules described herein, comprises data records storing various information that can be used to form one or more constraints to apply to certain functions and/or operations. For example, the information pertaining to a rule in the rule base might comprise the conditional logic operands (e.g., input variables, conditions, constraints, etc.) and/or operators (e.g., "if", "then", "and", "or", "greater than", "less than", etc.) for forming a conditional logic statement that returns one or more results. Specifically, the request parameters and/or the policy parameters might be applied to such conditional logic statements in protection rules 426 to determine the data protection scheme attributes.

The data protection schemes (e.g., data protection scheme $134_1$) generated by the herein disclosed techniques can implement various approaches to achieve the request-specific health data protection characteristics in accordance with respective participant-specific data protection policies. For example, certain differential privacy (DP) and locality-sensitive hashing (LSH) techniques facilitate a wide range of fine-grained data protection characteristics that can be specific to a particular data protection scheme, participant, and/or data access request. Moreover, these techniques facilitate the use of a broad range of data analysis techniques by the participants. Specifically, DP adjusts the level of protection by injecting "noise" (e.g., randomized data) into a data set to facilitate generation of inferences from a data set while preserving the privacy of any PII in the data. The amount of noise to inject can be determined without knowledge of the contents or size of the data set. Rather, the noise calculation can be performed based on other information, such as the participant's privacy budget for the data set and/or other information. Such differentially-private data sets allow participants to use any data analysis approach that best achieves their analysis objectives without being concerned that the selected approach might increase the potential for data leakage.

LSH techniques facilitate a high-probability mapping (e.g., by a hash function) of "similar" data items in a metric space to a particular "bucket" in a hash space. As a comparison, conventional and/or cryptographic hashing maps only identical data items to a particular bucket. As such, LSH can improve the performance of certain analysis techniques, such as distance-based inference techniques, when performed over protected (e.g., hashed, obfuscated, etc.) data.

As shown in FIG. 4, the data protection scheme attributes of a data protection scheme might specify how such DP and/or LSH techniques are to be applied to a health data set. Specifically, and as depicted in a set of select data protection scheme attributes 428 associated with data protection scheme $134_1$, the data protection scheme attributes associated with a particular data set or subset (e.g., stored and/or described in a "dataSet[ ]" object) might describe one or more hash functions to apply to the data set or subset (e.g., stored in a "hashFunctions[ ]" object). Additionally or alternatively, one or more differential privacy algorithms might be stored in an object (e.g., stored in a "DPalgorithms[ ]" object), which differential privacy algorithm might be configured to apply a particular differential privacy level (e.g., stored in a "DPlevel[ ]" object) to a data set or subset. Additionally, the "hashFunctions[ ]" object might describe, for example, a family of functions to perform LSH over a portion of a health data set to obfuscate that portion of the data. The discrete or continuous hash collision probabilities associated with the LSH functions might also be specified in the "hashFunctions[ ]" object. Other parameters necessary to perform LSH and/or other types of hashing or obfuscation over the health data set may also be specified in the "hashFunctions[ ]" object and/or may be specified in other data protection scheme attributes.

As another example, the "DPalgorithms[ ]" object might describe the algorithms (e.g., private projected histograms, etc.) to perform over a portion of a health data set to create a differentially-private version of that portion of data. Other parameters necessary to create differentially-private versions of a health data set may be specified in the "DPalgorithms[ ]" object and/or other data protection scheme attributes. Specifically, a participant's privacy budget as indicated in the "privacy" policy parameter of the participant's data protection policy might be stored in a "DPlevel[ ]" object and used to determine an amount of noise to inject in a differentially-private version of a health data set that is requested by the participant.

The foregoing discussions include techniques for applying the aforementioned data protection schemes to health data sets to generate sets of protected health data (e.g., step 225 of FIG. 2), which techniques and data are disclosed in further detail as follows.

Figure 5:
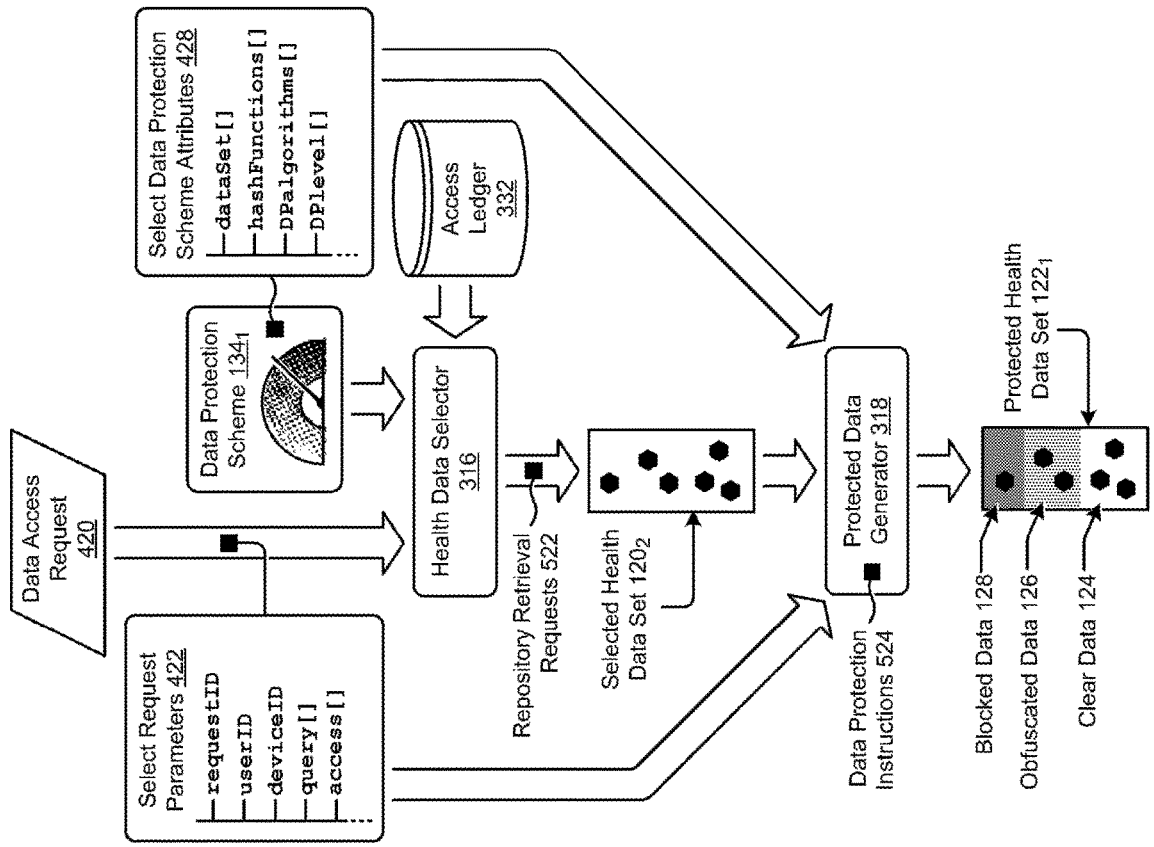
FIG. 5 presents a protected data generation technique as implemented in systems that facilitate dynamic determination of data protection schemes, according to an embodiment.
Figure 5:
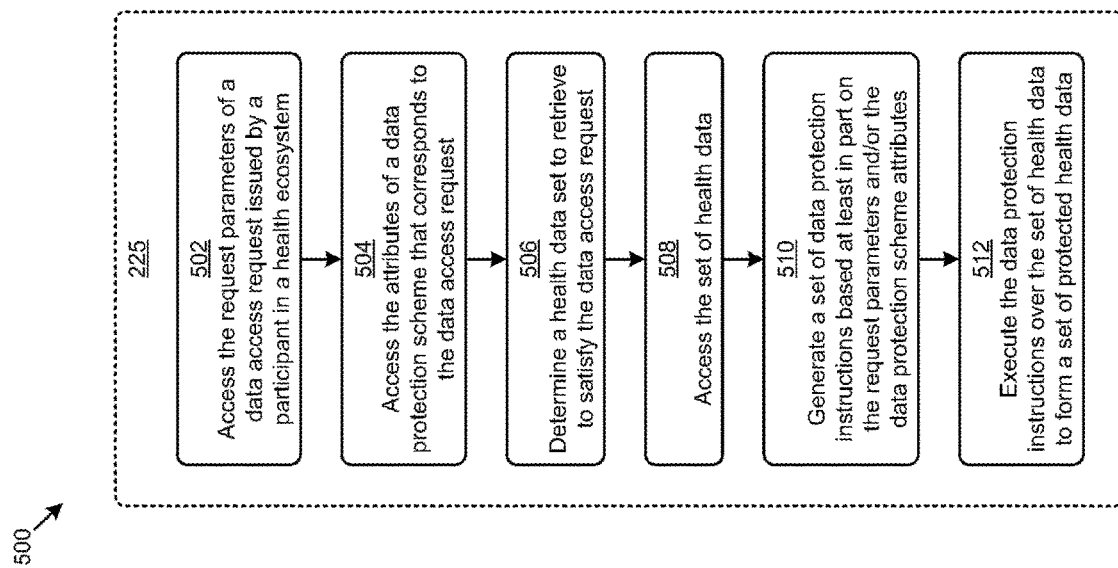

FIG. 5 presents a protected data generation technique 500 as implemented in systems that facilitate dynamic determination of data protection schemes. As an option, one or more variations of protected data generation technique 500 or any aspect thereof may be implemented in the context of the architecture and functionality of the embodiments described herein. The protected data generation technique 500 or any aspect thereof may be implemented in any environment.

FIG. 5 illustrates aspects pertaining to dynamically determining participant-specific policy-based data protection schemes to apply to data that is exchanged among various health ecosystem participants. Specifically, the figure is presented to illustrate one embodiment of certain steps and/or operations that facilitate applying a data protection scheme to a health data set to generate a set of protected health data (e.g., step 225 of FIG. 2). A representative protected health data set generation scenario is also shown in the figure to illustrate an example application of protected data generation technique 500.

Protected data generation technique 500 commences by accessing the request parameters of a data access request issued by a participant in a health ecosystem (step 502). For example, request parameters associated with data access request 420, such as those depicted by select request parameters 422, might be accessed. The attributes of a data protection scheme that corresponds to the data access request are also accessed (step 504). As shown, attributes associated with data protection scheme $134_1$ such as those depicted by select data protection scheme attributes 428 might be accessed.

Based at least in part on the aforementioned data access request parameters and data protection scheme attributes, a health data set that can satisfy the data access request is determined (step 506) and accessed (step 508). As can be observed, an instance of the health data selector 316 might access the data access request parameters and data protection scheme attributes to select, for example, particular selected health data sets 120 from the data repositories of various participants in the health ecosystem.

In some cases, certain information recorded in the access ledger 332 might be examined to determine the health data set to retrieve. For example, the health data set might be selected from the most accessed sets of repository data (e.g., as recorded in the access ledger 332) that are of a class corresponding to the class of the requested data. When the health data set and the corresponding data repositories are selected, health data selector 316 can invoke a set of repository retrieval requests 522 to retrieve the selected health data set 120, or merely identify certain attributes (e.g., location) of selected health data sets 120 for further operations, such as those discussed as follows.

A set of data protection instructions are generated based at least in part on the request parameters and/or the data protection scheme attributes (step 510). The data protection instructions are then executed over the health data set to form a set of protected health data (step 512). As can be observed in the shown representative scenario, an instance of protected data generator 318 accesses the request parameters and/or the data protection scheme attributes to generate a set of data protection instructions 524 that are executed over selected health data set $120_2$ to form the protected health data set $122_1$.

For example, the data protection instructions 524 might comprise instructions to perform certain hashing functions (e.g., LSH functions) and/or DP algorithms over one or more portions of selected health data set $120_2$ in accordance with constraints and/or parameters specified in the data protection scheme attributes. In some cases, some or all of the data protection instructions are performed over the selected health data set at the source data repositories prior to retrieval, whereas in other cases, some or all of the data protection instructions are performed over the selected health data set after retrieval from the source data repositories. As shown, the resulting protected health data set might comprise a first portion of blocked data 128, a second portion of obfuscated data 126, and third portion of clear data 124. As merely examples, clear data 124 might comprises certain text data (e.g., symptoms, etc.) and/or photographs (e.g., of a body part, etc.), and/or any other non-personally identifiable information (NPII).

The foregoing discussions include techniques for provisioning access to the sets of protected health data (e.g., step 226 of FIG. 2), which techniques and data are disclosed in further detail as follows.

Figure 6:
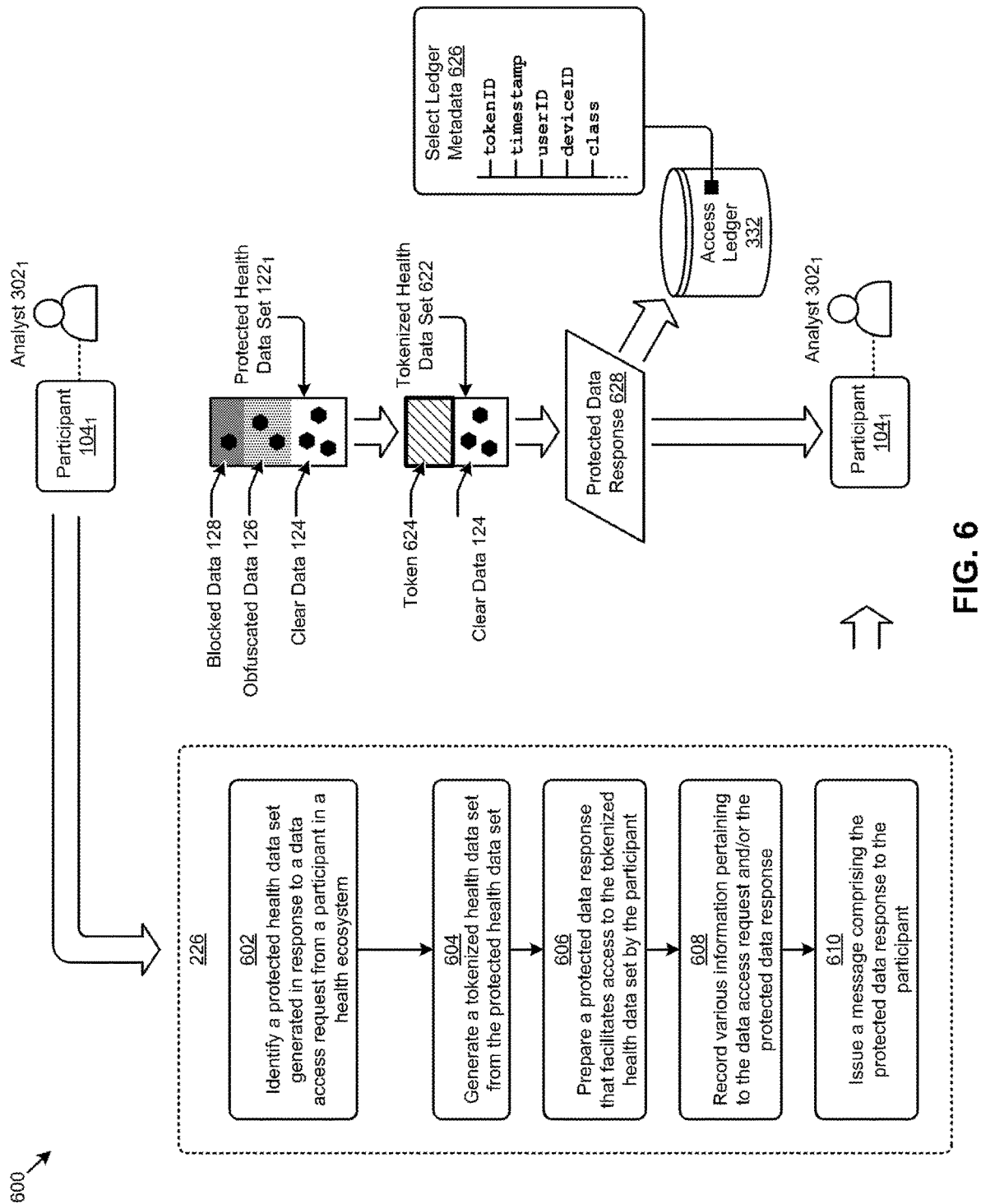
FIG. 6 depicts a protected health data delivery technique as implemented in systems that facilitate dynamic determination of data protection schemes, according to an embodiment.

FIG. 6 depicts a protected health data delivery technique 600 as implemented in systems that facilitate dynamic determination of data protection schemes. As an option, one or more variations of protected health data delivery technique 600 or any aspect thereof may be implemented in the context of the architecture and functionality of the embodiments described herein. The protected health data delivery technique 600 or any aspect thereof may be implemented in any environment.

FIG. 6 illustrates aspects pertaining to dynamically determining participant-specific policy-based data protection schemes to apply to data that is exchanged among various health ecosystem participants. Specifically, the figure is presented to illustrate one embodiment of certain steps and/or operations that facilitate provisioning access to the sets of protected health data generated according to the herein disclosed techniques (e.g., step 226 of FIG. 2). A representative protected health data delivery scenario is also shown in the figure to illustrate an example application of protected health data delivery technique 600.

Protected health data delivery technique 600 commences by identifying a protected health data set that is generated in response to a data access request from a participant in a health ecosystem (step 602). As shown, protected health data set 122$_1$ (e.g., comprising blocked data 128, obfuscated data 126, and clear data 124) might be generated in response to a request issued by an analyst 302$_1$ that is associated with participant 104$_1$. A tokenized health data set is generated from the protected health data set (step 604). For example, a token 624 might be generated from the obfuscated portion (e.g., obfuscated data 126) of protected health data set 122$_1$ so that, when combined with (e.g., prepended to) the clear data 124 of protected health data set 122$_1$, a tokenized health data set 622 is formed. In some cases, a token is formed from the portion of a health data set that is identified for obfuscation whereby that portion is obfuscated by the tokenization process itself. Various other techniques for generating the token 624 are possible. In some cases, a particular tokenization technique or algorithm is selected to serve a particular purpose. For example, tokenized health data set 622 may be generated using encryption and a security key so as to facilitate secure transmission of the portion of protected health data set 122$_1$ identified for obfuscation (e.g., the PII). In such cases, the participant receiving the tokenized health data set 622 might access a token security key service to receive a key, which key can then be used for decryption of the tokenized health data set.

A protected data response to facilitate access to the tokenized health data set by the participant is prepared (step 606). For example, a protected data response 628 might be prepared to facilitate access to tokenized health data set 622. Various information pertaining to the data access request and/or the protected data response associated with the participant is recorded (step 608). As can be observed, such information can be recorded in an instance of the access ledger 332 earlier described. Specifically, and as depicted in a representative set of select ledger metadata 626, a data record stored in access ledger 332 might describe a token identifier (e.g., stored in a "tokenID" field), a timestamp (e.g., stored in a "timestamp" field), a user or participant identifier (e.g., stored in a "userID" field), a user device identifier (e.g., stored in a "deviceID" field), a description of the data class corresponding to the health data set (e.g., stored in a "class" field), and/or other information pertaining to the data access request and/or an associated protected data response. The foregoing data records in the access ledger 332 can be organized and/or stored using various techniques (e.g., linked lists, relational database, etc.).

A message comprising the protected data response is then issued to the participant to facilitate access to the tokenized health data set (step 610). As an example, protected data response 628 is issued to participant 104$_1$ to provision access by analyst 302$_1$ to tokenized health data set 622. As earlier mentioned, the participant might interact with a token service to access the data underlying the tokenized portion of the tokenized health data set 622.

Additional Embodiments of the Disclosure

Additional Practical Application Examples

Figure 7:
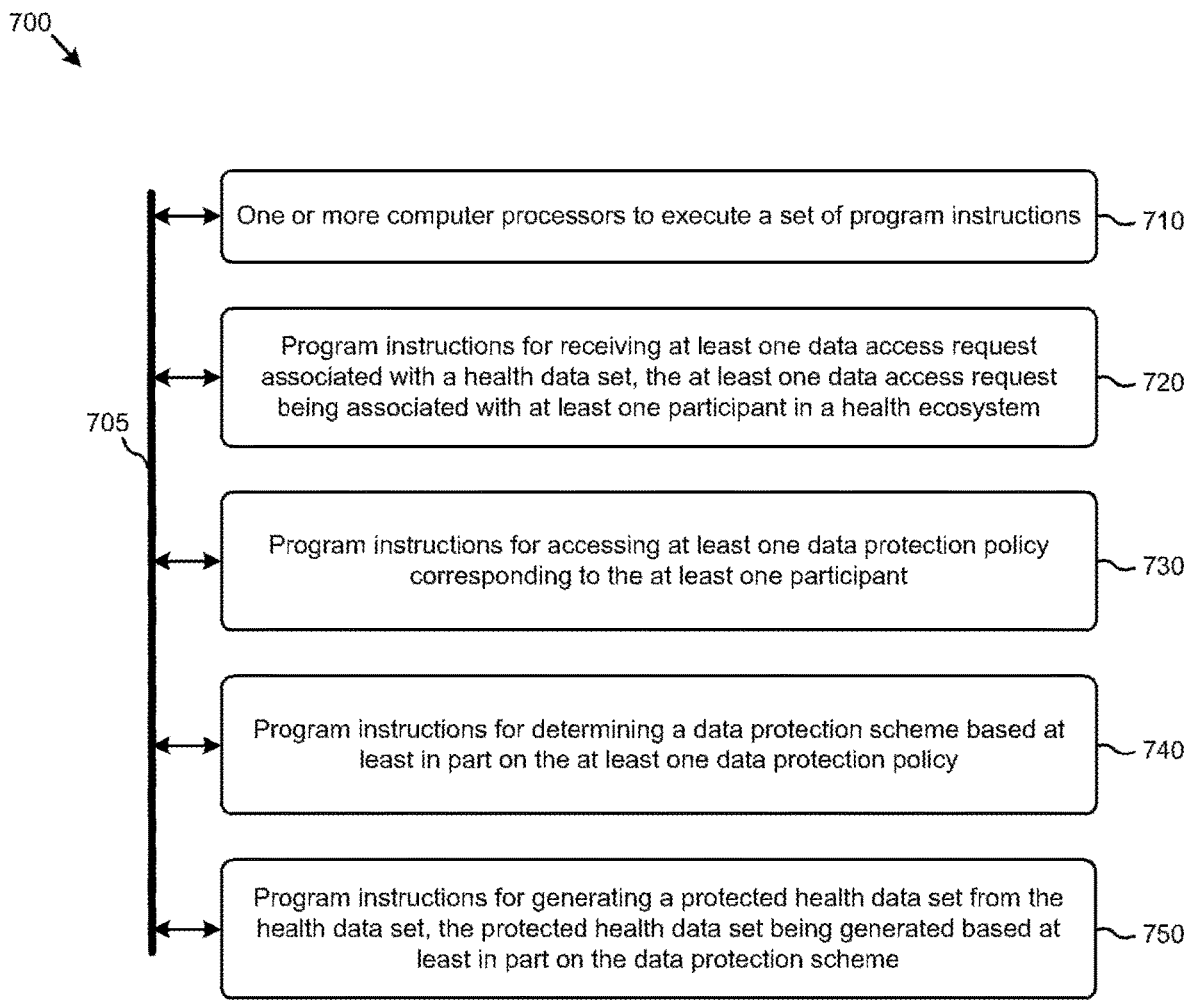
FIG. 7 depicts system components as arrangements of computing modules that are interconnected so as to implement certain of the herein-disclosed embodiments.

FIG. 7 depicts a system 700 as an arrangement of computing modules that are interconnected so as to operate cooperatively to implement certain of the herein-disclosed embodiments. This and other embodiments present particular arrangements of elements that, individually or as combined, serve to form improved technological processes that address determining a balance between the protection of data and the benefit derived from the data for a particular health ecosystem participant. The partitioning of system 700 is merely illustrative and other partitions are possible. As an option, the system 700 may be implemented in the context of the architecture and functionality of the embodiments described herein. Of course, however, the system 700 or any operation therein may be carried out in any desired environment.

The system 700 comprises at least one processor and at least one memory, the memory serving to store program instructions corresponding to the operations of the system. As shown, an operation can be implemented in whole or in part using program instructions accessible by a module. The modules are connected to a communication path 705, and any operation can communicate with any other operations over communication path 705. The modules of the system can, individually or in combination, perform method operations within system 700. Any operations performed within system 700 may be performed in any order unless as may be specified in the claims.

The shown embodiment implements a portion of a computer system, presented as system 700, comprising one or more computer processors to execute a set of program code instructions (module 710) and modules for accessing memory to hold program code instructions to perform: receiving at least one data access request associated with a health data set, the at least one data access request being associated with at least one participant in a health ecosystem (module 720); accessing at least one data protection policy corresponding to the at least one participant (module 730); determining a data protection scheme based at least in part on the at least one data protection policy (module 740); and generating a protected health data set from the health data set, the protected health data set being generated based at least in part on the data protection scheme (module 750).

Variations of the foregoing may include more or fewer of the shown modules. Certain variations may perform more or fewer (or different) steps and/or certain variations may use data elements in more, or in fewer, or in different operations. More particularly, some embodiments further comprise provisioning access to the protected health data set, the access to the protected health data set being provisioned to at least one participant by implementation of a network interface. Some embodiments further comprise selecting particular constituents of the health data set. In some cases, the health data set is selected based at least in part on characteristics of a data access request, and/or based on characteristics of a data protection policy, and/or based on characteristics of the various individual corpora where raw health data is stored.

In some cases, the data protection scheme is determined based on a privacy budget. The privacy budget can be derived from aspects of the data protection policy. In some cases, to achieve privacy metrics that comport with the aforementioned privacy budget and/or aspects of the data protection scheme, a differential privacy algorithm is applied to the health data. In addition to, or alternatively to applying a differential privacy algorithm in accordance with the data protection scheme, some portion of the health data set is blocked accordance with the data protection scheme and/or some portion of the health data set is obfuscated in accordance with the data protection scheme. In some cases, some portions of the health data set are obfuscated by a locality-sensitive hashing technique.

The foregoing data protection policy can be codified in a plurality of ways. As an example, a data structure might include one or more policy parameters that are associated with a policy identifier, and/or a participant identifier, and/or a user identifier, and/or an inference performance indicator, and/or a data leakage tolerance indicator, and/or other policy parameters.

The foregoing mechanisms might be implemented by computer processors and/or other operational elements (e.g., accelerators, hard-wired logic, machine learning engines, network components, etc.), Moreover, any of the foregoing operations or portions thereof may be performed at any location in the ecosystem where there are computer processors and/or other operational elements that can carry out instructions. As one particular example, a computer processor that is associated with an instance of a health data protection engine can perform a first set of instructions to carry out a portion of an operation, whereas a different computer processor that is associated with a participant can perform a second set of instructions to carry out a different portion of the operation. As such, in some embodiments, a processor that is associated with an instance of a health data protection engine can issue a set of instructions to cause an operational element of a participant to apply a participant-specific policy to the health data set. The resulting participant-specific protected health data that is generated by applying the participant-specific policy to the health data set can be stored in any location.

In some cases, the resulting participant-specific protected health data is stored at a participant-specific location such as in storage devices co-located with other operational elements of a participant, and/or the resulting participant-specific protected health data is stored in storage devices located at and/or managed by a cloud service. Access to the stored participant-specific protected health data can be implemented by providing a network address location of the participant-specific protected health data. In some cases, such access can be controlled in whole or in part by a computer processor that is associated with an instance of a health data protection engine. In other cases, such access can be controlled in whole or in part by operational elements of a participant. Still further, some embodiments include variations in the operations performed, and some embodiments include variations of aspects of the data elements used in the operations.

System Architecture Overview

Additional System Architecture Examples

Figure 8A:
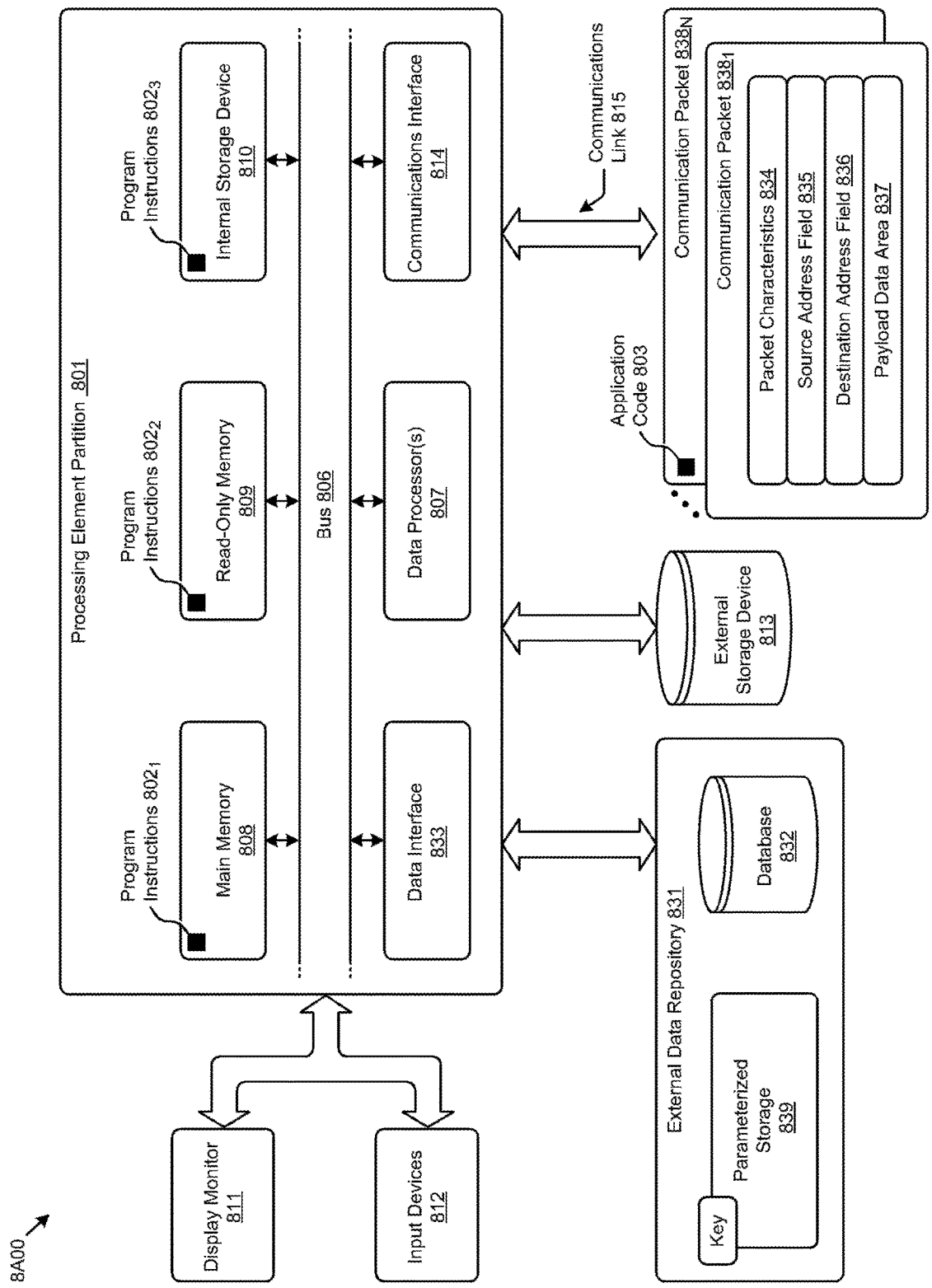
FIG. 8A and FIG. 8B present block diagrams of computer system architectures having components suitable for implementing embodiments of the present disclosure, and/or for use in the herein-described environments.

FIG. 8A depicts a block diagram of an instance of a computer system 8A00 suitable for implementing embodiments of the present disclosure. Computer system 8A00 includes a bus 806 or other communication mechanism for communicating information. The bus interconnects subsystems and devices such as a central processing unit (CPU), or a multi-core CPU (e.g., data processor 807), a system memory (e.g., main memory 808, or an area of random access memory (RAM)), a non-volatile storage device or non-volatile storage area (e.g., read-only memory 809), an internal storage device 810 or external storage device 813 (e.g., magnetic or optical), a data interface 833, a communications interface 814 (e.g., PHY, MAC, Ethernet interface, modem, etc.). The aforementioned components are shown within processing element partition 801, however other partitions are possible. Computer system 8A00 further comprises a display 811 (e.g., CRT or LCD), various input devices 812 (e.g., keyboard, cursor control), and an external data repository 831.

According to an embodiment of the disclosure, computer system 8A00 performs specific operations by data processor 807 executing one or more sequences of one or more program instructions contained in a memory. Such instructions (e.g., program instructions $802_1$, program instructions $802_2$, program instructions $802_3$, etc.) can be contained in or can be read into a storage location or memory from any computer readable/usable storage medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination thereof.

According to an embodiment of the disclosure, computer system 8A00 performs specific networking operations using one or more instances of communications interface 814. Instances of communications interface 814 may comprise one or more networking ports that are configurable (e.g., pertaining to speed, protocol, physical layer characteristics, media access characteristics, etc.) and any particular instance of communications interface 814 or port thereto can be configured differently from any other particular instance. Portions of a communication protocol can be carried out in whole or in part by any instance of communications interface 814, and data (e.g., packets, data structures, bit fields, etc.) can be positioned in storage locations within communications interface 814, or within system memory, and such data can be accessed (e.g., using random access addressing, or using direct memory access DMA, etc.) by devices such as data processor 807.

Communications link 815 can be configured to transmit (e.g., send, receive, signal, etc.) any types of communications packets (e.g., communication packet 838$_1$, communication packet 838$_N$) comprising any organization of data items. The data items can comprise a payload data area 837, a destination address 836 (e.g., a destination IP address), a source address 835 (e.g., a source IP address), and can include various encodings or formatting of bit fields to populate packet characteristics 834. In some cases, the packet characteristics include a version identifier, a packet or payload length, a traffic class, a flow label, etc. In some cases, payload data area 837 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to data processor 807 for execution. Such a medium may take many forms including, but not limited to, non-volatile media and volatile media. Non-volatile media includes, for example, optical or magnetic disks such as disk drives or tape drives. Volatile media includes dynamic memory such as RAM.

Common forms of computer readable media include, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of external data repository 831, which in turn can be formatted into any one or more storage areas, and which can comprise parameterized storage 839 accessible by a key (e.g., filename, table name, block address, offset address, etc.).

Execution of the sequences of instructions to practice certain embodiments of the disclosure are performed by a single instance of a computer system 8A00. According to certain embodiments of the disclosure, two or more instances of computer system 8A00 coupled by a communications link 815 (e.g., LAN, public switched telephone network, or wireless network) may perform the sequence of instructions required to practice embodiments of the disclosure using two or more instances of components of computer system 8A00.

Computer system 8A00 may transmit and receive messages such as data and/or instructions organized into a data structure (e.g., communications packets). The data structure can include program instructions (e.g., application code 803), communicated through communications link 815 and communications interface 814. Received program instructions may be executed by data processor 807 as it is received and/or stored in the shown storage device or in or upon any other non-volatile storage for later execution. Computer system 8A00 may communicate through a data interface 833 to a database 832 on an external data repository 831. Data items in a database can be accessed using a primary key (e.g., a relational database primary key).

Processing element partition 801 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a data processor 807. Some embodiments include one or more special-purpose hardware components (e.g., power control, logic, sensors, transducers, etc.). Some embodiments of a module include instructions that are stored in a memory for execution so as to facilitate operational and/or performance characteristics pertaining to dynamically determining data protection schemes. A module may include one or more state machines and/or combinational logic used to implement or facilitate the operational and/or performance characteristics pertaining to dynamically determining data protection schemes.

Various implementations of database 832 comprise storage media organized to hold a series of records or files such that individual records or files are accessed using a name or key (e.g., a primary key or a combination of keys and/or query clauses). Such files or records can be organized into one or more data structures (e.g., data structures used to implement or facilitate aspects of dynamically determining data protection schemes). Such files, records, or data structures can be brought into and/or stored in volatile or non-volatile memory. More specifically, the occurrence and organization of the foregoing files, records, and data structures improve the way that the computer stores and retrieves data in memory, for example, to improve the way data is accessed when the computer is performing operations pertaining to dynamically determining data protection schemes, and/or for improving the way data is manipulated when performing computerized operations pertaining to dynamically determining participant-specific policy-based data protection schemes to apply to data that is exchanged among various health ecosystem participants.

Figure 8B:
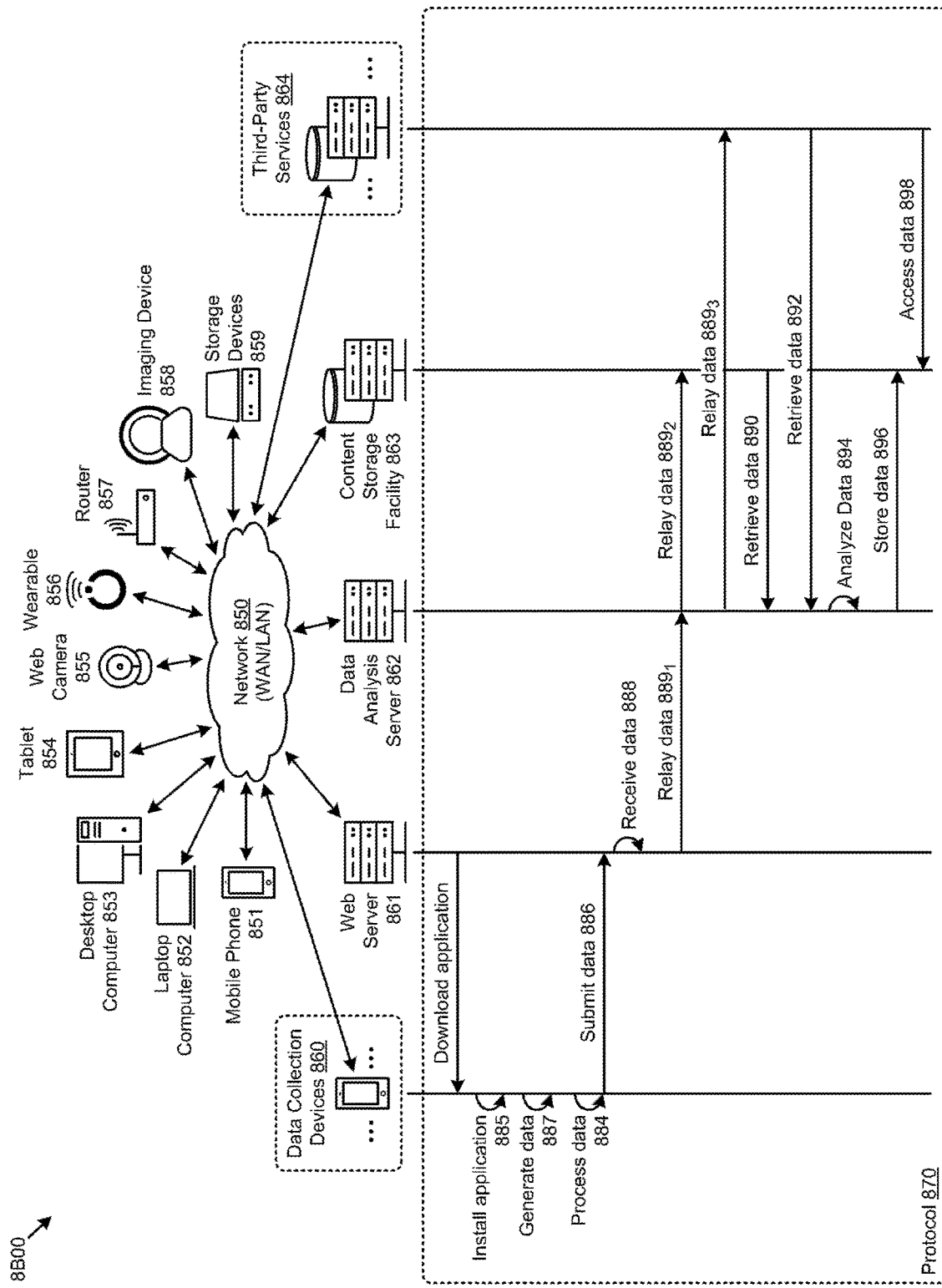

FIG. 8B depicts an environment 8B00 in which embodiments of the present disclosure can operate. As an option, one or more aspects shown in environment 8B00 or any combination of components of the environment may be implemented in the context of the architecture and functionality of the embodiments described herein.

As shown environment 8B00 comprises various computing systems (e.g., servers and devices) interconnected by a network 850. The network 850 can comprise any combination of a wide area network (e.g., WAN), local area network (e.g., LAN), cellular network, wireless LAN (e.g., WLAN), or any such means for enabling communication of computing systems. The network 850 can also be referred to as "the Internet" or as an "Internet". The example environment 8B00 comprises data collection devices 860, an instance of a web server 861, an instance of a data analysis server 862, a content storage facility 863, and optional instances of third-party services 864, which third-party services 864 may communicate with any other the other operational element over a network.

The servers and devices shown in environment 8B00 can represent any single computing system with dedicated hardware and software, or the servers and devices shown in environment 8B00 can represent multiple computing systems connected together (e.g., in a server farm, or in a host farm, etc.). In some cases, multiple computing systems share resources. For example, the web server 861 and the data analysis server 862 might be closely coupled (e.g., co-located) and/or might be implemented using the same hardware platform.

The environment 8B00 further comprises a variety of other devices such as a mobile phone 851, a laptop 852, a desktop computer 853, a tablet 854, a web camera 855, and a wearable device 856 etc. The environment further comprises computing equipment such as a router 857, an imaging device 858 (e.g., CT scanner, MRI machine, etc.), and any number of storage devices 859, etc. Some or all of the foregoing computing devices and computing equipment may support software (e.g., a browser, mobile application, etc.) and hardware (e.g., an LCD display, a graphics processing unit, display, monitor, etc.) capable of processing and displaying information (e.g., an image, a web page, etc.). Any of the foregoing computing devices or computing equipment can serve as one of the data collection devices 860.

In some embodiments, any particular one of the data collection devices 860 can be used in conjunction with a different particular one of the data collection devices to determine the location and/or identity of a user.

As shown, the computing devices and computing equipment can perform a set of high-level interactions (e.g., operations, messages, etc.) in a protocol 870. Specifically, the protocol can represent interactions in systems for measuring the quality of user-provided information.

An application or app can be generated using any known techniques. Such an application or app cooperates with other operational elements of the environment to perform operations pertaining to dynamically determining data protection schemes, and/or to perform computerized operations pertaining to dynamically determining participant-specific policy-based data protection schemes to apply to data that is exchanged among various health ecosystem participants. The application or app may be configured so as to operate on any one or more data collection device. As shown, any of the data collection devices 860 can download such an application or app from web server 861 and install the application (operation 885). The application can be used to capture and/or generate data (operation 887), process the captured or generated data (operation 884), and submit data to the web server (message 886).

To perform one or more operations of protocol 870, the web server is configured to receive data (operation 888) corresponding to the data submitted from the data collection devices. Such received data may be relayed or otherwise transmitted (message $889_1$, or message $889_2$, or message $889_3$) to downstream computing equipment such as data analysis server 862, and/or to a content storage facility 863, and/or to any one or more third-party services 864. Furthermore, the data analysis server may retrieve data (message 890) from any storage facility, including from content storage facility 863 or any one or more of the third-party services (message 892).

An instance of a data analysis server 862 can be configured to autonomously (e.g., under program control) analyze any received data (message 894). Moreover, example instances of a data analysis server 862 can be configured to store data (message 896) at any storage facility, including at content storage facility 863 or any one or more storage devices of third-party services.

In some cases, the third-party services produce additional data that is derived, directly or indirectly, from the data received from the data collection devices. In some cases, and as shown, such additional data might be still further retrieved (message 898) and analyzed by data analysis server 862. As such, data can be transformed in a cascading fashion. Specifically, data can be initially processed at the data collection device, then alternatively or additionally, the resulting data can be processed at the data analysis server, then alternatively or additionally, the still further resulting data can be processed at the third-party services.

In the foregoing specification, the disclosure has been described with reference to specific embodiments thereof. It will however be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are to be regarded in an illustrative sense rather than in a restrictive sense.

What is claimed is:

1. A method for dynamic data protection, the method comprising:
    receiving at least one data access request associated with a first data set, the at least one data access request being associated with at least one participant to access data that is exchanged over the Internet among two or more participants;
    accessing at least one data protection policy corresponding to the at least one participant;
    determining a data protection scheme based at least in part on parameter values corresponding to the at least one data protection policy;
    generating a protected data set from the first data set, the protected data set being generated based at least in part on application of a selected hashing algorithm; and
    provisioning access to the protected data set.

2. The method of claim 1, wherein the selected hashing algorithm comprises a locality-sensitive hashing technique.

3. The method of claim 1, further comprising:
    selecting the first data set wherein the selecting of the first data set is based at least in part on at least a first data protection policy; and
    selecting a second data set wherein the selecting of the second data set is based at least in part a second data protection policy.

4. The method of claim 1, wherein the data protection scheme is determined based at least in part on a privacy budget parameter, the privacy budget parameter being derived from the at least one data protection policy.

5. The method of claim 1, wherein at least one differential privacy algorithm is applied to the first data set in accordance with the data protection scheme.

6. The method of claim 1, wherein access to at least a portion of the first data set is blocked in accordance with the data protection scheme.

7. The method of claim 1, wherein at least a portion of the first data set is obfuscated in accordance with the data protection scheme.

8. The method of claim 7, wherein the portion of the first data set is obfuscated by a locality-sensitive hashing technique.

9. The method of claim 1, wherein the at least one data protection policy is characterized by one or more policy parameters, the one or more policy parameters being associated with at least one of, a policy identifier, a participant identifier, a user identifier, an inference performance indicator, or a data leakage tolerance indicator.

10. The method of claim 1, further comprising:
issuing a set of instructions to cause an operational element of the at least one participant to apply a participant-specific policy to the first data set.

11. The method of claim 10, further comprising:
storing participant-specific protected data after applying at least a portion of the participant-specific policy to the first data set.

12. The method of claim 11, further comprising:
selecting a second data set wherein the second data set is selected based at least in part a second data access request that is received after the applying of the at least a portion of the participant-specific policy to the first data set.

13. A non-transitory computer readable medium having stored thereon a sequence of instructions which, when stored in memory and executed by one or more processors causes the one or more processors to perform a set of acts for dynamic data protection, the set of acts comprising:
receiving at least one data access request associated with a first data set, the at least one data access request being associated with at least one participant to access data that is exchanged over the Internet among two or more participants;
accessing at least one data protection policy corresponding to the at least one participant;
determining a data protection scheme based at least in part on parameter values corresponding to the at least one data protection policy;
generating a protected data set from the first data set, the protected data set being generated based at least in part on application of a selected hashing algorithm; and
provisioning access to the protected data set.

14. The non-transitory computer readable medium of claim 13, wherein the selected hashing algorithm comprises a locality-sensitive hashing technique.

15. The non-transitory computer readable medium of claim 13, further comprising instructions which, when stored in memory and executed by the one or more processors causes the one or more processors to perform acts of:
selecting the first data set wherein the selecting of the first data set is based at least in part on at least a first data protection policy; and
selecting a second data set wherein the selecting of the second data set is based at least in part a second data protection policy.

16. The non-transitory computer readable medium of claim 13, wherein the data protection scheme is determined based at least in part on a privacy budget parameter, the privacy budget parameter being derived from the at least one data protection policy.

17. The non-transitory computer readable medium of claim 13, wherein at least one differential privacy algorithm is applied to the first data set in accordance with the data protection scheme.

18. A system for dynamic data protection, the system comprising:
a storage medium having stored thereon a sequence of instructions; and
one or more processors that execute the instructions to cause the one or more processors to perform a set of acts, the set of acts comprising:
receiving at least one data access request associated with a first data set, the at least one data access request being associated with at least one participant to access data that is exchanged over the Internet among two or more participants;
accessing at least one data protection policy corresponding to the at least one participant;
determining a data protection scheme based at least in part on parameter values corresponding to the at least one data protection policy;
generating a protected data set from the first data set, the protected data set being generated based at least in part on application of a selected hashing algorithm; and
provisioning access to the protected data set.

19. The system of claim 18, wherein the selected hashing algorithm comprises a locality-sensitive hashing technique.

20. The system of claim 18, further comprising instructions which, when stored in memory and executed by the one or more processors causes the one or more processors to perform acts of:
selecting the first data set wherein the selecting of the first data set is based at least in part on at least a first data protection policy; and
selecting a second data set wherein the selecting of the second data set is based at least in part a second data protection policy.

* * * * *